United States Patent
Xie et al.

(10) Patent No.: US 9,603,908 B2
(45) Date of Patent: Mar. 28, 2017

(54) SUBCUTANEOUS ADMINISTRATION OF IDURONATE-2-SULFATASE

(71) Applicant: SHIRE HUMAN GENETIC THERAPIES, INC., Lexington, MA (US)

(72) Inventors: Hongsheng Xie, Acton, MA (US); Brian Felice, Wellesley, MA (US); Thomas McCauley, Cambridge, MA (US)

(73) Assignee: Shire Human Genetic Therapies, Inc., Lexington, MA (US)

(*) Notice: Subject to any disclaimer, the term of this patent is extended or adjusted under 35 U.S.C. 154(b) by 0 days.

(21) Appl. No.: 14/389,058

(22) PCT Filed: Mar. 14, 2013

(86) PCT No.: PCT/US2013/031662
§ 371 (c)(1),
(2) Date: Sep. 29, 2014

(87) PCT Pub. No.: WO2013/148277
PCT Pub. Date: Oct. 3, 2013

(65) Prior Publication Data
US 2015/0086526 A1 Mar. 26, 2015

Related U.S. Application Data

(60) Provisional application No. 61/618,638, filed on Mar. 30, 2012.

(51) Int. Cl.
*A61K 38/46* (2006.01)
*A61K 9/00* (2006.01)

(52) U.S. Cl.
CPC .......... *A61K 38/465* (2013.01); *A61K 9/0019* (2013.01); *A61K 38/46* (2013.01); *C12Y 301/06013* (2013.01)

(58) Field of Classification Search
None
See application file for complete search history.

(56) References Cited

U.S. PATENT DOCUMENTS

| | | | |
|---|---|---|---|
| 5,728,381 A | 3/1998 | Wilson et al. | |
| 2005/0208090 A1 | 9/2005 | Keimel et al. | |
| 2011/0110935 A1 | 5/2011 | Pardridge et al. | |
| 2011/0318323 A1* | 12/2011 | Zhu | A61K 9/0085 424/94.3 |

FOREIGN PATENT DOCUMENTS

| | | |
|---|---|---|
| WO | WO 2005/113765 A2 | 12/2005 |
| WO | WO 2011/041897 A1 | 4/2011 |

OTHER PUBLICATIONS

Smith et al., Clinical Nursing Skills, 5th ed.; Prentice Hall Health: NJ, 2000; pp. 381-393.*
Da Silva et al., "Enzyme replacement therapy with idursulfase for mucopolysaccharidosis type II (Hunter syndrome)", Cochrane Database of Systematic Review 2011, Issue 11. Art. No. CD008185; pp. 1-25.*

* cited by examiner

*Primary Examiner* — Renee Claytor
*Assistant Examiner* — Michelle F Paguio Frising
(74) *Attorney, Agent, or Firm* — Fangli Chen; Prosauker Rose LLP

(57) ABSTRACT

The present invention provides, among other things, compositions, kits and methods for subcutaneous delivery of lysosomal enzymes for effective treatment of lysosomal storage diseases. In some embodiments, the present invention provides methods for treating Hunter syndrome by subcutaneous administration of a replacement iduronate-2-sulfatase (I2S) protein. In some embodiments, the present invention provides a kit comprising an arrangement of components for subcutaneously administering iduronate-2-sulfatase (I2S) protein.

24 Claims, 15 Drawing Sheets

SUBCUTANEOUS ADMINISTRATION OF IDURONATE-2-SULFATASE

CROSS REFERENCE TO RELATED APPLICATIONS

This application is the 35 U.S.C. §371 National Stage of International Application No. PCT/US2013/031662, filed Mar. 14, 2013, which claims priority to U.S. Provisional Application No. 61/618,638, filed Mar. 30, 2012, the contents of both of which are incorporated herein by reference in their entirety.

SEQUENCE LISTING

The present specification makes reference to a Sequence Listing submitted in electronic form as an ASCII .txt file named "2006685-0291_SEQ_LIST" on Mar. 14, 2013. The .txt file was generated on Mar. 6, 2013 and is 17 KB in size.

BACKGROUND OF THE INVENTION

Mucopolysaccharidosis type II (MPS II, Hunter syndrome) is an X-chromosome-linked recessive lysosomal storage disorder that results from a deficiency in the enzyme iduronate-2-sulfatase (I2S). I2S cleaves the terminal 2-O-sulfate moieties from the glycosaminoglycans (GAG) dermatan sulfate and heparan sulfate. Due to the missing or defective I2S enzyme in patients with Hunter syndrome, GAG progressively accumulate in the lysosomes of a variety of cell types, leading to cellular engorgement, organomegaly, tissue destruction, and organ system dysfunction.

Generally, physical manifestations for people with Hunter syndrome include both somatic and neuronal symptoms. For example, in some cases of Hunter syndrome, central nervous system involvement leads to developmental delays and nervous system problems. While the non-neuronal symptoms of Hunter Syndrome are generally absent at birth, over time the progressive accumulation of GAG in the cells of the body can have a dramatic impact on the peripheral tissues of the body. GAG accumulation in the peripheral tissue leads to a distinctive coarseness in the facial features of a patient and is responsible for the prominent forehead, flattened bridge and enlarged tongue, the defining hallmarks of a Hunter patient. Similarly, the accumulation of GAG can adversely affect the organ systems of the body. Manifesting initially as a thickening of the wall of the heart, lungs and airways, and abnormal enlargement of the liver, spleen and kidneys, these profound changes can ultimately lead to widespread catastrophic organ failure. As a result, Hunter syndrome is always severe, progressive, and life-limiting.

Enzyme replacement therapy (ERT) is an approved therapy for treating Hunter syndrome (MPS II), which involves administering exogenous replacement I2S enzyme to patients with Hunter syndrome.

SUMMARY OF THE INVENTION

The present invention relates to improved enzyme replacement therapy for lysosomal storage disease, in particular, Hunter syndrome. The present invention provides methods for delivering replacement I2S enzyme by subcutaneous administration. This invention is, in part, based on the surprising discovery that subcutaneous administration of replacement I2S enzyme results in unexpectedly high bioavailability (e.g., the maximum achievable bioavailability) and better pharmacokinetic parameters of replacement I2S protein in vivo as compared to intravenous administration. This unexpected effect allows for more effective systematic delivery of I2S to various target tissues, resulting in improved efficacy. In addition, enzymatic replacement therapy based on subcutaneous administration may significantly improve patients' quality of life. For example, subcutaneous administration avoids prolonged infusion, frequent visitation to clinics or hospitalization, typically required by intravenous administration. As the subcutaneous administration retains the same bioavailability of the i.v. form, but has a higher concentration, it may allow for a different dosing schema including a less frequent administration. By contrast, to achieve less frequent i.v. administration, it requires that the replacement enzyme be administered at a higher dose and/or by a prolonged infusion, which is undesirable for patients and caregivers. Subcutaneous administration based enzyme replacement therapy may also make it possible for patients to self-administer I2S without the need for direct professional care during the administration. Therefore, the present invention provides a highly efficient, clinically desirable and patient-friendly approach for Hunter syndrome treatment and represents a significant advancement in the field of enzyme replacement therapy.

In one aspect, the present invention provides a method for treating Hunter syndrome comprising administering subcutaneously to a subject suffering from or susceptible to Hunter syndrome a therapeutically effective dose of a replacement iduronate-2-sulfatase (I2S) protein periodically at an administration interval such that at least one symptom or feature of Hunter syndrome is reduced in intensity, severity, or frequency, or has delayed onset. In some embodiments, the step of administering subcutaneously comprises administering the replacement I2S protein at a subcutaneous tissue selected from thigh region, abdominal region, gluteal region, upper arm or scapular region of the subject.

In some embodiments, the therapeutically effective dose is in a range from about 0.5 mg/kg to 20 mg/kg body weight (e.g., from about 0.5 mg/kg to 15 mg/kg, from about 0.5 mg/kg to 10 mg/kg, from about 0.5 mg/kg to 5 mg/kg, from about 0.5 mg/kg to 2.5 mg/kg).

In some embodiments, the therapeutically effective dose is sufficient to achieve serum concentration of the replacement I2S protein within a range from about 10 ng/ml to 10,000 ng/ml (e.g., from about 10 ng/ml to 8,000 ng/ml, from about 10 ng/ml to 6,000 ng/ml, from about 10 ng/ml to 4,000 ng/ml, from about 10 ng/ml to 2,000 ng/ml, from about 100 ng/ml to 10,000 ng/ml, from about 100 ng/ml to 8,000 ng/ml, from about 100 ng/ml to 6,000 ng/ml, from about 100 ng/ml to 4,000 ng/ml, from about 100 ng/ml to 2,000 ng/ml) within 24 hours following administration to the subject.

In some embodiments, the therapeutically effective dose is sufficient to achieve the average maximum serum concentration ($C_{max}$) following a single administration of greater than about 1.5 µg/ml (e.g., greater than about 2.0 µg/ml, 2.5 µg/ml, 3.0 µg/ml, 3.5 µg/ml, 4.0 µg/ml, 4.5 µg/ml, 5.0 µg/ml, or more).

In some embodiments, the therapeutically effective dose is sufficient to achieve the average area under the concentration-time curve (AUC) following a single administration of greater than about 200 min*µg/ml (e.g., greater than about 250 min*µg/ml, 300 min*µg/ml, 350 min*µg/ml, 400 min*µg/ml, 450 min*µg/ml, 500 min*µg/ml, 550 min*µg/ml, 600 min*µg/ml, 650 min*µg/ml, 700 min*µg/ml, 750 min*µg/ml, 800 min*µg/ml, 850 min*µg/ml, 900 min*µg/ml, 950 min*µg/ml, 1,000 min*µg/ml, or more).

In some embodiments, the administration interval is daily, three times a week, twice a week, weekly, bi-weekly, monthly, once every two months, once every three months, once every four months, once every five months, once every six months, or at a variable intervals. In some embodiments, the administration interval is longer than a week, two weeks, three weeks, four weeks, a month, two months, three months, four months, five months, or six months.

In some embodiments, the replacement I2S protein is administered in a volume of or less than about 5 ml (e.g., less than about 4.5 ml, 4.0 ml, 3.5 ml, 3.0 ml, 2.5 ml, 2.0 ml, 1.5 ml, 1.0 ml, 0.5 ml).

In some embodiments, the replacement I2S protein is administered at a concentration ranging from approximately 1-300 µg/ml (e.g., approximately 1-250 µg/ml, 1-200 mg/ml, 1-150 mg/ml, 1-100 mg/ml, 1-50 mg/ml, 1-25 mg/ml, 1-20 mg/ml). In some embodiments, the replacement I2S protein is administered at a concentration of or greater than 2 mg/ml (e.g., of or greater than 5 mg/ml, 10 mg/ml, 15 mg/ml, 20 mg/ml, 25 mg/ml, 30 mg/ml, 35 mg/ml, 40 mg/ml, 45 mg/ml, 50 mg/ml, 75 mg/ml, 100 mg/ml, 125 mg/ml, 150 mg/ml, 200 mg/ml, 250 mg/ml, 300 mg/ml).

In some embodiments, the replacement I2S protein is administered in a saline solution. In some embodiments, a suitable saline solution contains sodium chloride. In some embodiments, the sodium chloride is present at a concentration ranging from approximately 0-2% (e.g., from approximately 0-1.5% or 0-1.0%). In some embodiments, the sodium chloride is present at a concentration of approximately 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0%.

In some embodiments, a suitable saline solution contains a surfactant. In some embodiments, the surfactant is selected from the group consisting of polysorbate 20, polysorbate 40, polysorbate 60, polysorbate 80 and combinations thereof. In some embodiments, the surfactant is polysorbate 20. In some embodiments, the polysorbate 20 is present at a concentration ranging from approximately 0-0.2% (e.g., 0-0.15%, 0-0.1%, 0-0.08%, 0-0.06%, 0-0.04%, 0-0.02%, or 0-0.01%).

In some embodiments, a suitable saline solution has a pH ranging from approximately 3-8 (e.g., from approximately 4-7.0, 5.0-7.0, 5.0-6.5, 5.5-6.5, or 6.0-7.0). In some embodiments, a suitable saline solution has a pH of approximately 5.0, 5.5, 5.6, 5.7, 5.8, 5.9, 6.0, 6.1, 6.2, 6.3, 6.4, 6.5, 6.8, or 7.0.

In some embodiments, the step of subcutaneous administration results in systemic delivery of the replacement I2S protein in one or more target tissues. In some embodiments, the one or more target tissues are selected from muscle, skin, liver, kidney, spleen, joints, bone, lung and airways, tongue, upper respiratory tract, eye, ear, connective tissue and/or heart.

In some embodiments, the step of subcutaneous administration results in increased I2S protein enzymatic level and/or activity in the one or more target tissues (e.g., muscle, skin, liver, kidney, spleen, joints, bone, lung and airways, tongue, upper respiratory tract, eye, ear, connective tissue and/or heart). In some embodiments, the I2S enzymatic level or activity in the one or more target tissues is increased by at least 1-fold, 2-fold, 3-fold, 4-fold, 5-fold, 6-fold, 7-fold, 8-fold, 9-fold or 10-fold as compared to a control (e.g., the I2S enzymatic level or activity of pre-treatment state or of an untreated control). In some embodiments, the increased enzymatic activity in the one or more target tissues is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg. In some embodiments, the increased enzymatic level or activity in the one or more target tissues is at least approximately 10% (e.g., at least approximately 15%, 20%, 25%, 30%, 35%, 40%, 45%, 50%, 55%, 60%, 65%, 70%, 75%, 80%, 85%, 90%, or 95%) of normal I2S enzymatic level or activity.

In some embodiments, the step of subcutaneous administration results in reduction of GAG level in serum, urine or target tissues (e.g., muscle, skin, liver, kidney, spleen, joints, bone, lung and airways, tongue, upper respiratory tract, eye, ear, connective tissue and/or heart). In some embodiments, the GAG level is reduced by at least 20%, 40%, 50%, 60%, 80%, 90%, 1-fold, 1.5-fold, or 2-fold as compared to a control (e.g., the GAG level of pre-treatment state or of an untreated control). In some embodiments, the step of subcutaneous administration results in reduced size of liver and/or spleen. In some embodiments, the size of liver and/or spleen is reduced by at least 10%, 20%, 40%, 50%, 60%, 80%, 90%, 1-fold, 1.5-fold, or 2-fold as compared to a control (e.g., the size of pre-treatment state or of an untreated control).

In some embodiments, the step of subcutaneous administration results in improved walking capacity in the subject. In some embodiments, the walking capacity is improved by, on average, at least 10 meters, 15 meters, 20 meters, 25 meters, 30 meters, 35 meters, 40 meters, 45 meters, 50 meters, 55 meters, 60 meters, 65 meters, 70 meters, 75 meters, 80 meters, 85 meters, 90 meters, 95 meters, 100 meters, 110 meters, 120 meters, 130 meters, 140 meters, 150 meters, 160 meters, 170 meters, 180 meters, 190 meters, 200 meters, 210 meters, 220 meters, 230 meters, 240 meters, 250 meters, or more as determined by the 6-Minute Walk Test as compared to a control. In some embodiments, the walking capacity is improved by, on average, 10%, 20%, 30%, 40%, 50%, 60%, 70%, 80%, 90%, 1-fold, 2-fold, 3-fold, 4-fold, 5-fold, 6-fold, 7-fold, 8-fold, 9-fold, 10-fold, or more as determined by the 6-Minute Walk Test as compared to a control.

In some embodiments, inventive methods according to the present invention further include administering the replacement I2S protein intrathecally and/or intravenously to the subject. In some embodiments, the intrathecal or intravenous administration is no more frequent than monthly administration (e.g., no more frequent than once every two months, once every three months, once every four months, once every five months, or once every six months). In certain embodiments, the intrathecal or intravenous administration is more frequent than monthly administration, such as twice weekly, weekly, every other week, or twice monthly. In some embodiments, the subcutaneous and intravenous or intrathecal administrations are performed on the same day. In some embodiments, the subcutaneous and intravenous or intrathecal administrations are not performed within a certain amount of time of each other, such as not within at least 2 days, within at least 3 days, within at least 4 days, within at least 5 days, within at least 6 days, within at least 7 days, within at least one week, within at least two weeks, within at least three weeks, or within at least a month. In some embodiments, the subcutaneous and intravenous or intrathecal administrations are performed on an alternating schedule, such as alternating administrations weekly, every other week, twice monthly, or monthly. In some embodiments, the subcutaneous and intravenous or intrathecal administrations are performed sequentially, such as performing intravenous or intrathecal administrations first (e.g., weekly, every other week, twice monthly, or monthly dosing for two weeks, a month, two months, three months, four months, five months, six months, or a year or more) followed by subcutaneous administrations (e.g., weekly, every other week, twice monthly, or monthly dosing for more than two weeks, a month, two months, three months, four months, five months, six months, or a year or more). In some embodiments, subcutaneous administrations are performed first (e.g., weekly, every other week, twice monthly, monthly, once every two months, once every three months dosing for two weeks, a month, two months, three months, four months, five months, six months, or a year or more) followed by intravenous or intrathecal administrations (e.g., weekly, every other week, twice monthly, or monthly dosing for more than two weeks, a month, two months, three months, four months, five months, six months, or a year or more).

In some embodiments, the replacement I2S protein is produced recombinantly. In some embodiments, the I2S protein is produced from a nucleic acid, such as, but not limited to, DNA, RNA (e.g., mRNA). In some embodiments, the replacement I2S protein is produced from mammalian cells. In some embodiments, suitable mammalian cells are human cells. In some embodiments, the replacement I2S protein is produced from mammalian cells that have increased expression of formylglycine generating enzyme (FGE).

In some embodiments, a suitable replacement I2S protein comprises amino acid sequences of SEQ ID NO:1.

In another aspect, the present invention provides various kits suitable to carry out inventive methods described herein. In some embodiments, a kit according to the invention includes a container containing a single dosage form of a replacement I2S protein; and a device for subcutaneous administration. In some embodiments, the single dosage form of the replacement I2S protein is provided in a liquid solution. In some embodiments, the single dosage form of the replacement I2S protein is provided as lyophilized powder. In some embodiments, a kit according to the invention further includes a saline solution for dilution or re-constitution of the replacement I2S protein. In some embodiments, a suitable container is selected from an ampule, a vial, a cartridge, a reservoir, a lyo-ject, or a pre-filled syringe. In certain embodiments, the container is a pre-filled syringe. In certain particular embodiments, the pre-filled syringe is selected from borosilicate glass syringes with baked silicone coating, borosilicate glass syringes with sprayed silicone, or plastic resin syringes without silicone. In some embodiments, the device for subcutaneous administration includes a needle and/or syringe. In some embodiments, a kit according to the invention further includes an instruction for self-administration.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF DRAWINGS

The drawings are for illustration purposes only not for limitation.

DEFINITIONS

Figure 1:
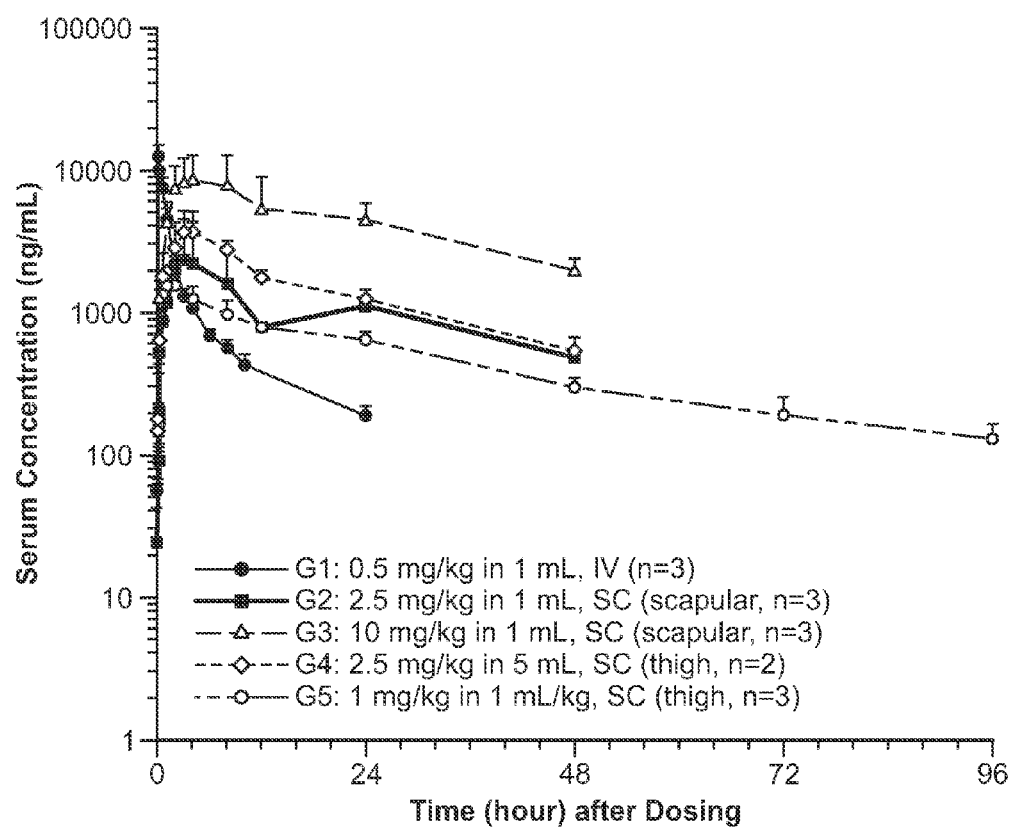
FIG. 1 illustrates exemplary data comparing the mean serum concentrations (±SD) as a function of time in non-human primates (NHPs), for five different experimental treatment groups (G1-G5).
Figure 2:
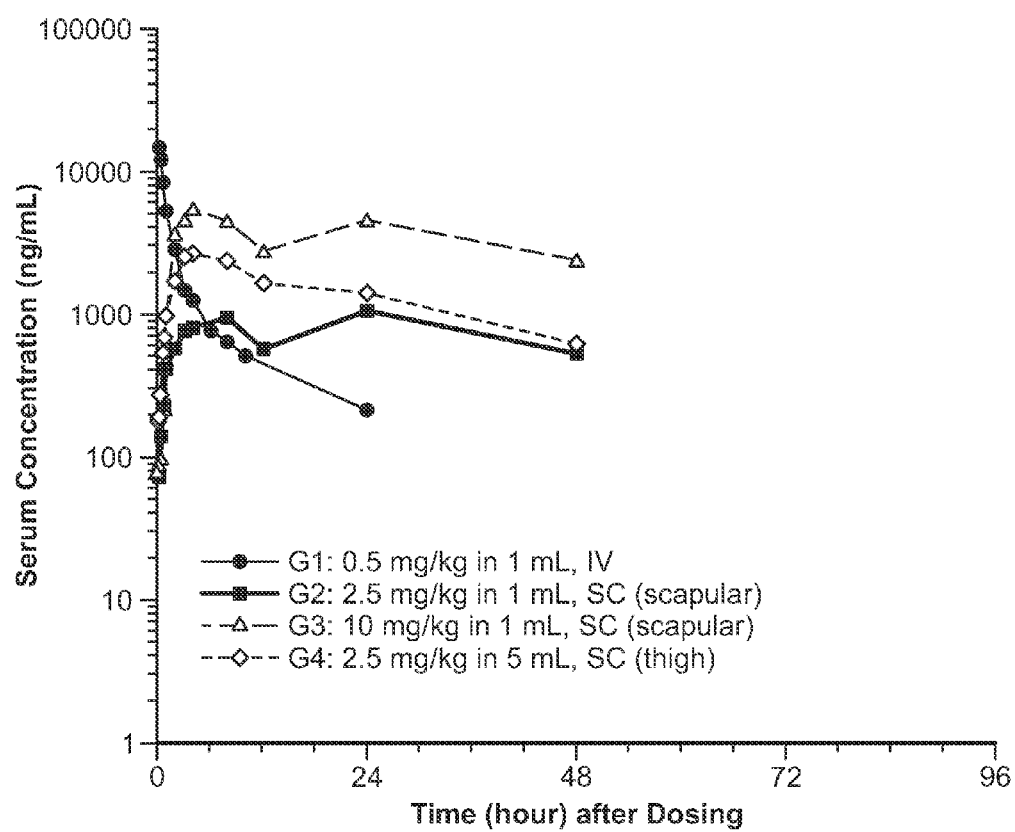
FIG. 2 illustrates exemplary data comparing serum concentration as a function of time in non-human primate 5303, following intravenous (IV) or subcutaneous (SC) treatment at various concentrations.
Figure 3:
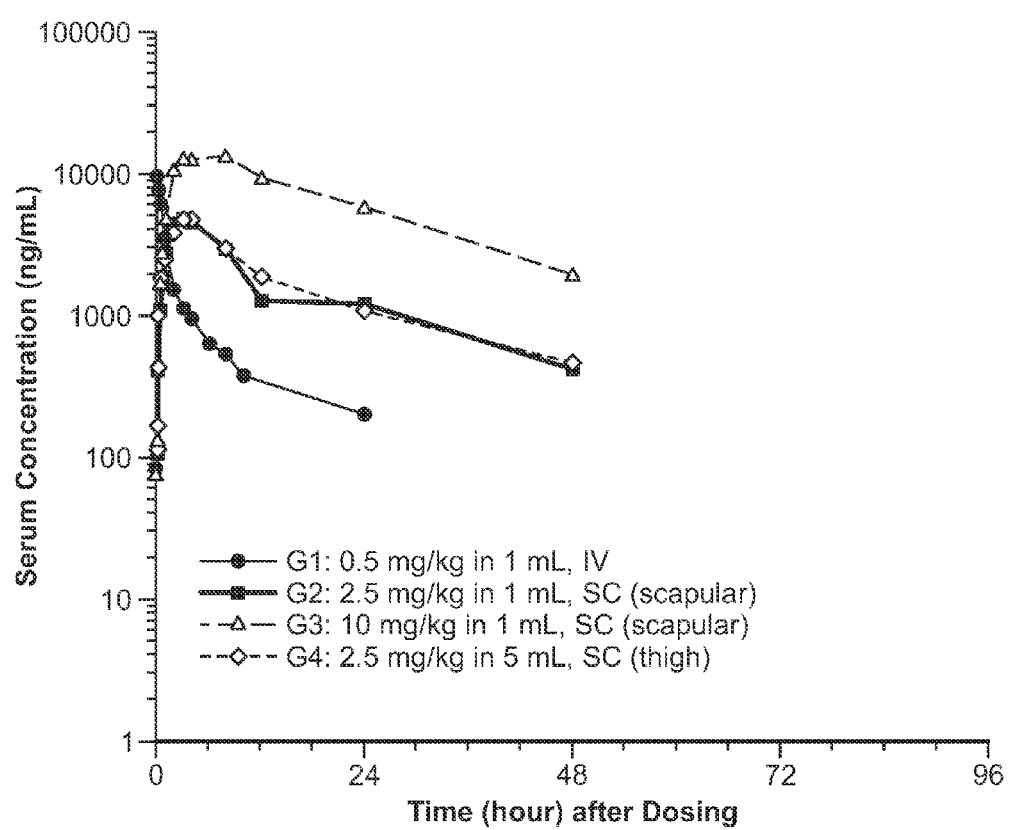
FIG. 3 illustrates exemplary data comparing serum concentration as a function of time in non-human primate 5306, following intravenous (IV) or subcutaneous (SC) treatment at various concentrations.
Figure 4:
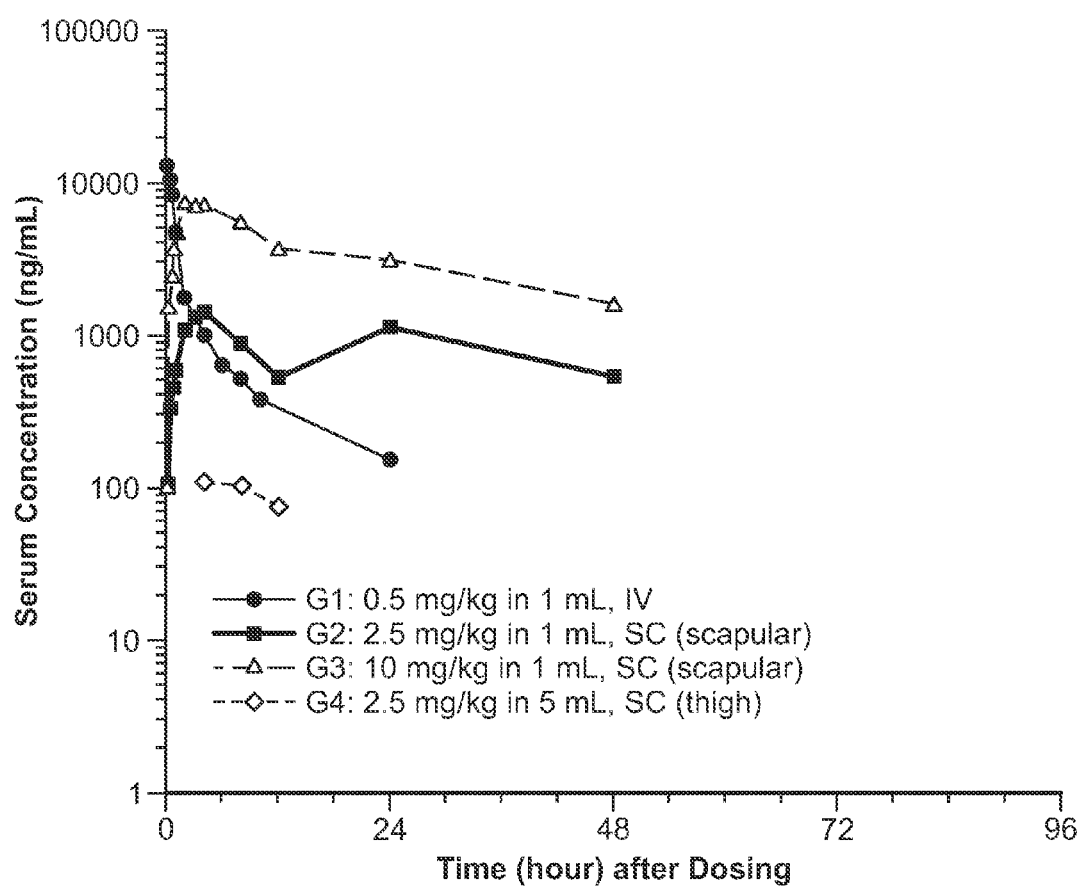
FIG. 4 illustrates exemplary data comparing serum concentration as a function of time in non-human primate 5324, following intravenous (IV) or subcutaneous (SC) treatment at various concentrations.
Figure 5:
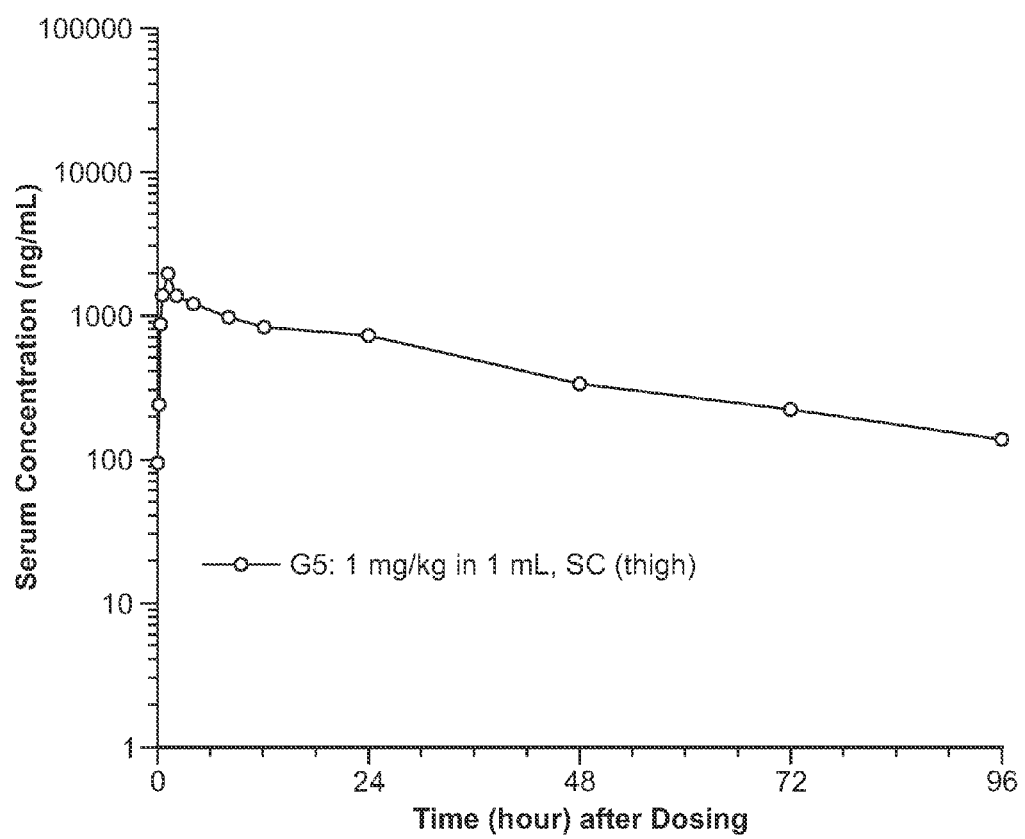
FIG. 5 illustrates exemplary data comparing serum concentration as a function of time in non-human primate 5319, following intravenous (IV) or subcutaneous (SC) treatment at various concentrations.
Figure 6:
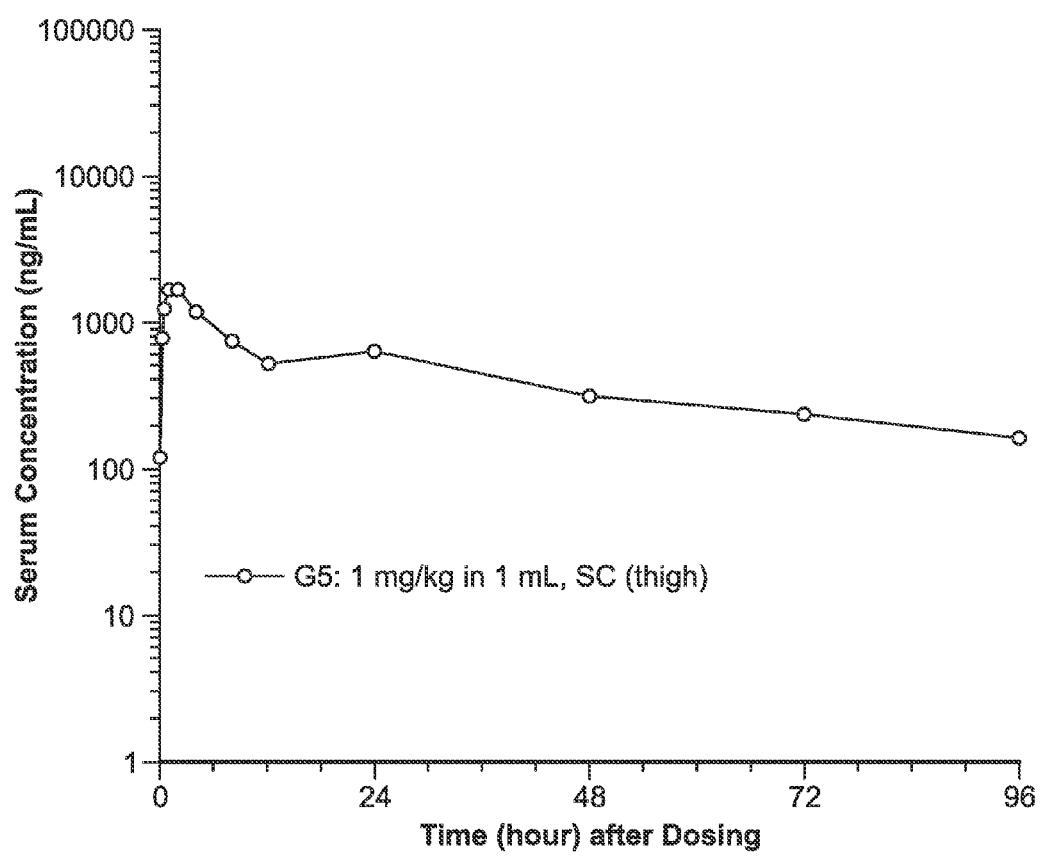
FIG. 6 illustrates exemplary data comparing serum concentration as a function of time in non-human primate 5265, following intravenous (IV) or subcutaneous (SC) treatment at various concentrations.
Figure 7:
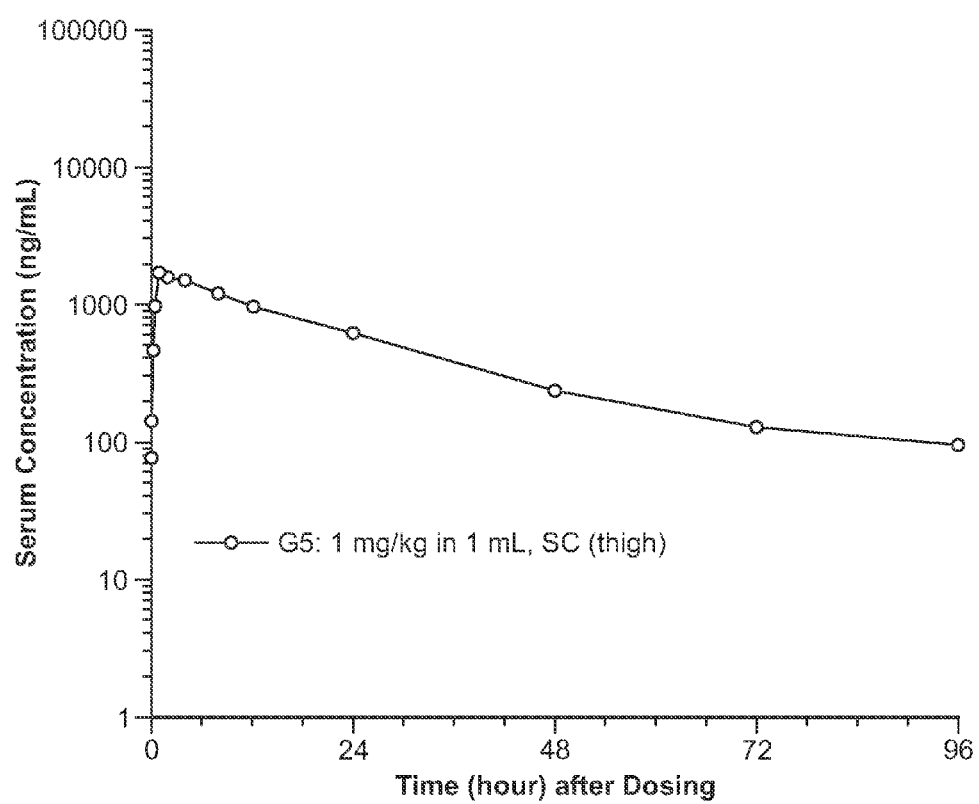
FIG. 7 illustrates exemplary data comparing serum concentration as a function of time in non-human primate 5363, following intravenous (IV) or subcutaneous (SC) treatment at various concentrations.

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Bioavailability: As used herein, the term "bioavailability" generally refers to the percentage of the administered dose that reaches the blood stream of a subject.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Bulking agent: As used herein, the term "bulking agent" refers to a compound which adds mass to the lyophilized mixture and contributes to the physical structure of the lyophilized cake (e.g., facilitates the production of an essentially uniform lyophilized cake which maintains an open pore structure). Exemplary bulking agents include mannitol, glycine, sodium chloride, hydroxyethyl starch, lactose, sucrose, trehalose, polyethylene glycol and dextran.

Concurrent immunosuppressant therapy: As used herein, the term "concurrent immunosuppressant therapy" includes any immunosuppressant therapy used as pre-treatment, pre-conditioning or in parallel to a treatment method.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic protein for the patient to be treated. Each unit contains a predetermined quantity of active material calculated to produce the desired therapeutic effect. It will be understood, however, that the total dosage of the composition will be decided by the attending physician within the scope of sound medical judgment.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into bloodstream. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Excipient: As used herein, the term "excipient" refers to any inert substance added to a drug and/or formulation for the purposes of improving its physical qualities (i.e. consistency), pharmacokinetic properties (i.e. bioavailabity), pharmacodynamic properties and combinations thereof.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a disease.

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Lyoprotectant: As used herein, the term "lyoprotectant" refers to a molecule that prevents or reduces chemical and/or physical instability of a protein or other substance upon lyophilization and subsequent storage. Exemplary lyoprotectants include sugars such as sucrose or trehalose; an amino acid such as monosodium glutamate or histidine; a methylamine such as betaine; a lyotropic salt such as magnesium sulfate: a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. In some embodiments, a lyoprotectant is a non-reducing sugar, such as trehalose or sucrose.

Lysosomal enzyme: As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the invention include both wild-type or modified lysosomal enzymes and can be produced using recombinant and synthetic methods or purified from nature sources. Exemplary lysosomal enzymes are listed in Table 1.

Lysosomal enzyme deficiency: As used herein, "lysosomal enzyme deficiency" refers to a group of genetic disorders that result from deficiency in at least one of the enzymes that are required to break macromolecules (e.g., enzyme substrates) down to peptides, amino acids, monosaccharides, nucleic acids and fatty acids in lysosomes. As a result, individuals suffering from lysosomal enzyme deficiencies have accumulated materials in various tissues (e.g., CNS, liver, spleen, gut, blood vessel walls and other organs).

Lysosomal Storage Disease: As used herein, the term "lysosomal storage disease" refers to any disease resulting from the deficiency of one or more lysosomal enzymes necessary for metabolizing natural macromolecules. These diseases typically result in the accumulation of un-degraded molecules in the lysosomes, resulting in increased numbers of storage granules (also termed storage vesicles). These diseases and various examples are described in more detail below.

Peripheral Target Tissue: As used herein, the tem "peripheral target tissue" refers to any aggregation of similarly specialized cells which together form certain special functions of the body and constitute a structure, organ or organ system of the body excluding the central nervous system and are separated by the blood brain barrier.

Pharmaceutically acceptable carrier: As used herein, the term "pharmaceutically acceptable carrier" includes any and all solvents, salts, diluents, emulsifiers, dispersion media, buffers and other components. The phrase "pharmaceutically-acceptable" also refers to any entity or composition that does not produce an undesirable allergic or antigenic response when administered to a subject.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Replacement enzyme: As used herein, the term "replacement enzyme" refers to any enzyme that can act to replace at least in part the deficient or missing enzyme in a disease to be treated. In some embodiments, the term "replacement enzyme" refers to any enzyme that can act to replace at least in part the deficient or missing lysosomal enzyme in a lysosomal storage disease to be treated. In some embodiments, a replacement enzyme is capable of reducing accumulated materials in mammalian lysosomes or that can rescue or ameliorate one or more lysosomal storage disease symptoms. Replacement enzymes suitable for the invention include both wild-type or modified lysosomal enzymes and can be produced using recombinant and synthetic methods or purified from nature sources. A replacement enzyme can be a recombinant, synthetic, gene-activated or natural enzyme.

Soluble: As used herein, the term "soluble" refers to the ability of a therapeutic agent to form a homogenous solution. In some embodiments, the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts). In some embodiments, the pharmaceutical compositions are formulated such that calcium salts are excluded from such compositions. In some embodiments, therapeutic agents in accordance with the present invention are soluble in its corresponding pharmaceutical composition. It will be appreciated that, while isotonic solutions are generally preferred for parenterally administered drugs, the use of isotonic solutions may limit adequate solubility for some therapeutic agents and, in particular some proteins and/or enzymes. Slightly hypertonic solutions (e.g., up to 175 mM sodium chloride in 5 mM sodium phosphate at pH 7.0) and sugar-containing solutions (e.g., up to 2% sucrose in 5 mM sodium phosphate at pH 7.0) have been demonstrated to be well tolerated in monkeys. For example, the most common approved CNS bolus formulation composition is saline (150 mM NaCl in water).

Stability: As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In general, pharmaceutical compositions described herein have been formulated such that they are capable of stabilizing, or alternatively slowing or preventing the degradation, of one or more therapeutic agents formulated therewith (e.g., recombinant proteins). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Subject: As used herein, the term "subject" means any mammal, including humans. In certain embodiments of the present invention the subject is an adult, an adolescent or an infant. Also contemplated by the present invention are the administration of the pharmaceutical compositions and/or performance of the methods of treatment in-utero.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids. and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., Methods in Enzymology; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suitable for Subcutaneous delivery: As used herein, the phrase "suitable for Subcutaneous delivery" or "suitable for subcutaneous delivery" as it relates to the pharmaceutical compositions of the present invention generally refers to the stability, tolerability, and solubility properties of such compositions, as well as the ability of such compositions to deliver an effective amount of the therapeutic agent contained therein to the targeted site of delivery.

Target tissues: As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. Exemplary target tissues are described in detail below.

Therapeutic moiety: As used herein, the term "therapeutic moiety" refers to a portion of a molecule that renders the therapeutic effect of the molecule. In some embodiments, a therapeutic moiety is a polypeptide having therapeutic activity.

Therapeutically effective amount: As used herein, the term "therapeutically effective amount" refers to an amount of a therapeutic protein (e.g., replacement enzyme) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Tolerable: As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Treatment: As used herein, the term "treatment" (also "treat" or "treating") refers to any administration of a therapeutic protein (e.g., lysosomal enzyme) that partially or completely alleviates, ameliorates, relieves, inhibits, delays onset of, reduces severity of and/or reduces incidence of one or more symptoms or features of a particular disease, disorder, and/or condition (e.g., Hunters syndrome). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION OF INVENTION

The present invention provides, among other things, improved methods, compositions and kits for effective treatment of Hunter syndrome based on subcutaneous administration of replacement I2S enzyme.

In various embodiments, the present invention provides a method for treating Hunter syndrome comprising administering subcutaneously to a subject suffering from or susceptible to Hunter syndrome a therapeutically effective dose of a replacement iduronate-2-sulfatase (I2S) protein periodically at an administration interval such that at least one symptom or feature of Hunter syndrome is reduced in intensity, severity, or frequency, or has delayed onset. Subcutaneous administration according to the present invention may be used alone, or in conjunction, with other administration modes such as intravenous and/or intrathecal administration.

The present invention provides various unexpected and beneficial features that allow efficient and convenient delivery of replacement I2S enzymes to various target tissues, resulting in effective treatment of Hunter syndrome.

Various aspects of the invention are described in detail in the following sections. The use of sections is not meant to limit the invention. Each section can apply to any aspect of the invention. In this application, the use of "or" means "and/or" unless stated otherwise.

Replacement I2S Enzyme

A replacement I2S enzyme suitable for the present invention can be any molecule or a portion of a molecule that can substitute for at least partial activity of naturally-occurring Iduronate-2-sulfatase (I2S) protein or rescue one or more phenotypes or symptoms associated with I2S-deficiency. In some embodiments, a replacement enzyme suitable for the invention is a polypeptide having an amino acid sequence substantially similar or identical to mature human I2S protein. As used herein, the terms "replacement I2S enzyme" and "replacement I2S protein", and grammatical equivalents, are used inter-changeably.

Typically, the human I2S protein is produced as a precursor form. The precursor form of human I2S contains a signal peptide (amino acid residues 1-25 of the full length precursor), a pro-peptide (amino acid residues 26-33 of the full length precursor), and a chain (residues 34-550 of the full length precursor) that may be further processed into the 42 kDa chain (residues 34-455 of the full length precursor) and the 14 kDa chain (residues 446-550 of the full length precursor). Typically, the precursor form is also referred to as full-length precursor or full-length I2S protein, which contains 550 amino acids. The amino acid sequences of the mature form (SEQ ID NO:1) having the signal peptide removed and full-length precursor (SEQ ID NO:2) of a typical wild-type or naturally-occurring human I2S protein are shown in Table 1. The signal peptide is underlined. In addition, the amino acid sequences of human I2S protein isoform a and b precursor are also provided in Table 1, SEQ ID NO:3 and 4, respectively.

TABLE 1

Human Iduronate-2-sulfatase

| | |
|---|---|
| Mature Form | SETQANSTTDALNVLLIIVDDLRPSLGCYGDKLVRSPNI DQLASHSLLFQNAFAQQAVCAPSRVSFLTGRRPDTTRLY DFNSYWRVHAGNFSTIPQYFKENGYVTMSVGKVFHPGIS SNHTDDSPYSWSFPPYHPSSEKYENTKTCRGPDGELHAN LLCPVDVLDVPEGTLPDKQSTEQATQLLEKMKTSASPFF LAVGYHKPHIPFRYPKEFQKLYPLENITLAPDPEVPDGL PPVAYNPWMDIRQREDVQALNISVPYGPIPVDFQRKIRQ SYFASVSYLDTQVGRLLSALDDLQLANSTITAFTSDHGW ALGEHGEWAKYSNFDVATHVPLIFYVPGRTASLPEAGEK LFPYLDPFDSASQLMEPGRQSMDLVELVSLFPTLAGLAG LQVPPRCPVPSFHVELCREGKNLLKHFRFRDLEEDPYLP GNPRELIAYSQYPRPSDIPQWNSDKPSLKDIKIMGYSIR TIDYRYTVWVGFNPDEFLANFSDIHAGELYFVDSDPLQD HNMYNDSQGGDLFQLLMP (SEQ ID NO: 1) |
| Full-Length Precursor (Isoform a) | MPPPRTGRGLLWLGLVLSSVCVALGSETQANSTTDALNV LLIIVDDLRPSLGCYGDKLVRSPNIDQLASHSLLFQNAF AQQAVCAPSRVSFLTGRRPDTTRLYDFNSYWRVHAGNFS TIPQYFKENGYVTMSVGKVFHPGISSNHTDDSPYSWSFP PYHPSSEKYENTKTCRGPDGELHANLLCPVDVLDVPEGT LPDKQSTEQAIQLLEKMKTSASPFFLAVGYHKPHIPFRY PKEFQKLYPLENITLAPDPEVPDGLPPVAYNPWMDIRQR EDVQALNISVPYGPIPVDFQRKIRQSYFASVSYLDTQVG RLLSALDDLQLANSTITAFTSDHGWALGEHGEWAKYSNF DVATHVPLIFYVPGRTASLPEAGEKLFPYLDPFDSASQL MEPGRQSMDLVELVSLFPTLAGLAGLQVPPRCPVPSFHV ELCREGKNLLKHFRFRDLEEDPYLPGNPRELIAYSQYPR PSDIPQWNSDKPSLKDIKIMGYSIRTIDYRYTVWVGFNP DEFLANFSDIHAGELYFVDSDPLQDHNMYNDSQGGDLFQ LLMP (SEQ ID NO: 2) |
| Isoform b Precursor | MPPPRTGRGLLWLGLVLSSVCVALGSETQANSTTDALNV LLIIVDDLRPSLGCYGDKLVRSPNIDQLASHSLLFQNAF AQQAVCAPSRVSFLTGRRPDTTRLYDFNSYWRVHAGNFS TIPQYFKENGYVTMSVGKVFHPGISSNHTDDSPYSWSFP PYHPSSEKYENTKTCRGPDGELHANLLCPVDVLDVPEGT LPDKQSTEQATQLLEKMKTSASPFFLAVGYHKPHIPFRY PKEFQKLYPLENITLAPDPEVPDGLPPVAYNPWMDIRQR EDVQALNISVPYGPIPVDFQRKIRQSYFASVSYLDTQVG RLLSALDDLQLANSTITAFTSDHGWALGEHGEWAKYSNF DVATHVPLIFYVPGRTASLPEAGEKLFPYLDPFDSASQL MEPGRQSMDLVELVSLFPTLAGLAGLQVPPRCPVPSFHV ELCREGKNLLKHFRFRDLEEDPYLPGNPRELIAYSQYPR PSDIPQWNSDKPSLKDIKIMGYSIRTIDYRYTVWVGFNP DEFLANFSDIHAGELYFVDSDPLQDHNMYNDSQGGDLFQ LLMP (SEQ ID NO: 3) |
| Isoform c Precursor | MPPPRTGRGLLWLGLVLSSVCVALGSETQANSTTDALNV LLIIVDDLRPSLGCYGDKLVRSPNIDQLASHSLLFQNAF AQQAVCAPSRVSFLTGRRPDTTRLYDFNSYWRVHAGNFS TIPQYFKENGYVTMSVGKVFHPGISSNHTDDSPYSWSFP PYHPSSEKYENTKTCRGPDGELHANLLCPVDVLDVPEGT LPDKQSTEQATQLLEKMKTSASPFFLAVGYHKPHIPFRY PKEFQKLYPLENITLAPDPEVPDGLPPVAYNPWMDIRQR EDVQALNISVPYGPIPVDFQRKIRQSYFASVSYLDTQVG RLLSALDDLQLANSTIIAFTSDHGFLMRTNT (SEQ ID No: 4) |

Thus, in some embodiments, a replacement enzyme suitable for the present invention is mature human I2S protein (SEQ ID NO:1). As disclosed herein, SEQ ID NO:1 represents the canonical amino acid sequence for the human I2S protein. In some embodiments, the I2S protein may be a splice isoform and/or variant of SEQ ID NO:1, resulting from transcription at an alternative start site within the 5' UTR of the I2S gene. In some embodiments, a suitable replacement enzyme may be a homologue or an analogue of mature human I2S protein. For example, a homologue or an analogue of mature human I2S protein may be a modified mature human I2S protein containing one or more amino acid substitutions, deletions, and/or insertions as compared to a wild-type or naturally-occurring I2S protein (e.g., SEQ ID NO:1), while retaining substantial I2S protein activity. Thus, in some embodiments, a replacement enzyme suitable for the present invention is substantially homologous to mature human I2S protein (SEQ ID NO:1). In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a replacement enzyme suitable for the present invention is substantially identical to mature human I2S protein (SEQ ID NO:1). In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a replacement enzyme suitable for the present invention contains a fragment or a portion of mature human I2S protein.

Alternatively, a replacement enzyme suitable for the present invention is full-length I2S protein. In some embodiments, a suitable replacement enzyme may be a homologue or an analogue of full-length human I2S protein. For example, a homologue or an analogue of full-length human I2S protein may be a modified full-length human I2S protein containing one or more amino acid substitutions, deletions, and/or insertions as compared to a wild-type or naturally-occurring full-length I2S protein (e.g., SEQ ID NO:2), while retaining substantial I2S protein activity. Thus, In some embodiments, a replacement enzyme suitable for the present invention is substantially homologous to full-length human I2S protein (SEQ ID NO:2). In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, a replacement enzyme suitable for the present invention is substantially identical to SEQ ID NO:2. In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, a replacement enzyme suitable for the present invention contains a fragment or a portion of full-length human I2S protein. As used herein, a full-length I2S protein typically contains signal peptide sequence.

In some embodiments, a replacement enzyme suitable for the present invention is human I2S isoform a protein. In some embodiments, a suitable replacement enzyme may be a homologue or an analogue of human I2S isoform a protein. For example, a homologue or an analogue of human I2S isoform a protein may be a modified human I2S isoform a protein containing one or more amino acid substitutions, deletions, and/or insertions as compared to a wild-type or naturally-occurring human I2S isoform a protein (e.g., SEQ ID NO:3), while retaining substantial I2S protein activity. Thus, In some embodiments, a replacement enzyme suitable for the present invention is substantially homologous to human I2S isoform a protein (SEQ ID NO:3). In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:3. In some embodiments, a replacement enzyme suitable for the present invention is substantially identical to SEQ ID NO:3. In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:3. In some embodiments, a replacement enzyme suitable for the present invention contains a fragment or a portion of human I2S isoform a protein. As used herein, a human I2S isoform a protein typically contains a signal peptide sequence.

In some embodiments, a replacement enzyme suitable for the present invention is human I2S isoform b protein. In some embodiments, a suitable replacement enzyme may be a homologue or an analogue of human I2S isoform b protein. For example, a homologue or an analogue of human I2S isoform b protein may be a modified human I2S isoform b protein containing one or more amino acid substitutions, deletions, and/or insertions as compared to a wild-type or naturally-occurring human I2S isoform b protein (e.g., SEQ ID NO:4), while retaining substantial I2S protein activity. Thus, In some embodiments, a replacement enzyme suitable for the present invention is substantially homologous to human I2S isoform b protein (SEQ ID NO:4). In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:4. In some embodiments, a replacement enzyme suitable for the present invention is substantially identical to SEQ ID NO:4. In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:4. In some embodiments, a replacement enzyme suitable for the present invention contains a fragment or a portion of human I2S isoform b protein. As used herein, a human I2S isoform b protein typically contains a signal peptide sequence.

Homologues or analogues of human I2S proteins can be prepared according to methods for altering polypeptide sequence known to one of ordinary skill in the art such as are found in references that compile such methods. In some embodiments, conservative substitutions of amino acids include substitutions made among amino acids within the following groups: (a) M, I, L, V; (b) F, Y, W; (c) K, R, H; (d) A, G; (e) S, T; (f) Q, N; and (g) E, D. In some embodiments, a "conservative amino acid substitution" refers to an amino acid substitution that does not alter the relative charge or size characteristics of the protein in which the amino acid substitution is made.

Production of Replacement I2S Enzymes

A replacement I2S protein or enzyme suitable for the present invention may be produced by any available means. For example, replacement enzymes may be recombinantly produced by utilizing a host cell system engineered to express a replacement enzyme-encoding nucleic acid. Alternatively or additionally, replacement enzymes may be produced by activating endogenous genes. Alternatively or additionally, replacement enzymes may be partially or fully prepared by chemical synthesis. Alternatively or additionally, replacements enzymes may also be purified from natural sources.

Where enzymes are recombinantly produced, any expression system can be used. To give but a few examples, known expression systems include, for example, egg, baculovirus, plant, yeast, or mammalian cells.

In some embodiments, enzymes suitable for the present invention are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651); human embryonic kidney line (HEK293 or 293 cells subcloned for growth in suspension culture, Graham et al., J. Gen Virol., 36:59, 1977); human fibrosarcoma cell line (e.g., HT1080); baby hamster kidney cells (BHK21, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, inventive methods according to the present invention are used to deliver replacement enzymes produced from human cells. In some embodiments, inventive methods according to the present invention are used to deliver replacement enzymes produced from CHO cells.

Typically, cells that are engineered to express recombinant I2S may comprise a transgene that encodes a recombinant I2S protein described herein. It should be appreciated that the nucleic acids encoding recombinant I2S may contain regulatory sequences, gene control sequences, promoters, non-coding sequences and/or other appropriate sequences for expressing the recombinant I2S. Typically, the coding region is operably linked with one or more of these nucleic acid components.

"Regulatory sequences" typically refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences. Sometimes, "regulatory sequences" are also referred to as "gene control sequences."

"Promoter" typically refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions.

The "3' non-coding sequences" typically refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The "translation leader sequence" or "5' non-coding sequences" typically refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

Typically, the term "operatively linked" refers to the association of two or more nucleic acid fragments on a single nucleic acid fragment so that the function of one is affected by the other. For example, a promoter is operatively linked with a coding sequence when it is capable of affecting the expression of that coding sequence (i.e., that the coding sequence is under the transcriptional control of the promoter). Coding sequences can be operatively linked to regulatory sequences in sense or antisense orientation.

The coding region of a transgene may include one or more silent mutations to optimize codon usage for a particular cell type. For example, the codons of an I2S transgene may be optimized for expression in a vertebrate cell. In some embodiments, the codons of an I2S transgene may be optimized for expression in a mammalian cell. In some embodiments, the codons of an I2S transgene may be optimized for expression in a human cell.

Activation of Replacement I2S Enzymes

Typically, a replacement I2S enzyme suitable for the present invention is activated by the post-translational modification of a conserved cysteine (corresponding to amino acid 59 of mature human I2S) to formylglycine, also known as 2-amino-3-oxopropionic acid, or oxo-alanine. Such post-translational modification can be carried out by an enzyme known as Formylglycine Generating Enzyme (FGE). Thus, in some embodiments, replacement I2S enzymes suitable for the present invention are produced in cells that also express FGE protein. In particular embodiments, replacement I2S enzymes suitable for the present invention are produced in cells that have increased or enhanced expression of FGE protein. For example, cells may be engineered to over-express FGE in combination with recombinant I2S to facilitate the production of I2S preparations having high levels of active enzyme. In some embodiments, over-expression of FGE is achieved by expression (e.g., over-expression) of an exogenous FGE using standard recombinant technology. In some embodiments, over-expression of FGE is achieved by activated or enhanced expression of an endogenous FGE by, for example, activating or enhancing the promoter of the endogenous FGE gene. In some cases, the nucleic acid encoding recombinant I2S and the nucleic acid encoding a recombinant FGE protein are linked by a nucleic acid (e.g., a spacer sequence) having a sequence corresponding to an internal ribosomal entry site.

Any FGE having ability to convert cysteine to formylglycine may be used in the present invention. Exemplary nucleic acid and amino acid sequences for FGE proteins are disclosed in US 2004-0229250, the entire contents relating to such sequences and the sequences themselves are incorporated herein by reference in their entireties. It should be appreciated that the nucleic acids encoding recombinant FGE may comprise regulatory sequences, gene control sequences, promoters, non-coding sequences and/or other appropriate sequences for expressing the FGE. Typically, the coding region is operably linked with one or more of these nucleic acid components.

Lysosomal Targeting Moiety of Replacement I2S Enzymes

In some embodiments, replacement enzymes delivered using a method of the invention contain a moiety that binds to a receptor on the surface of target cells to facilitate cellular uptake and/or lysosomal targeting. For example, such a receptor may be the cation-independent mannose-6-phosphate receptor (CI-MPR) which binds the mannose-6-phosphate (M6P) residues. In addition, the CI-MPR also binds other proteins including IGF-II. In some embodiments, a replacement enzyme suitable for the present invention contains M6P residues on the surface of the protein. In some embodiments, a replacement enzyme suitable for the present invention may contain bis-phosphorylated oligosaccharides which have higher binding affinity to the CI-MPR. In some embodiments, a suitable enzyme contains up to about an average of about at least 20% bis-phosphorylated oligosaccharides per enzyme. In other embodiments, a suitable enzyme may contain about 10%, 15%, 18%, 20%, 25%, 30%, 35%, 40%, 45%, 50%, 55%, 60% bis-phosphorylated oligosaccharides per enzyme. While such bis-phosphorylated oligosaccharides may be naturally present on the enzyme, it should be noted that the enzymes may be modified to possess such oligosaccharides. For example, suitable replacement enzymes may be modified by certain enzymes which are capable of catalyzing the transfer of N-acetylglucosamine-L-phosphate from UDP-GlcNAc to the 6' position of α-1,2-linked mannoses on lysosomal enzymes. Methods and compositions for producing and using such enzymes are described by, for example, Canfield et al. in U.S. Pat. No. 6,537,785, and U.S. Pat. No. 6,534,300, each incorporated herein by reference.

In some embodiments, replacement enzymes for use in the present invention may be conjugated or fused to a lysosomal targeting moiety that is capable of binding to a receptor on the surface of target cells. A suitable lysosomal targeting moiety can be IGF-I, IGF-II, RAP, p97, and variants, homologues or fragments thereof (e.g., including those peptide having a sequence at least 70%, 75%, 80%, 85%, 90%, or 95% identical to a wild-type mature human IGF-I, IGF-II, RAP, p97 peptide sequence). The lysosomal targeting moiety may be conjugated or fused to an I2S protein or enzyme at the N-terminus, C-terminus or internally.

Formulations

Typically, suitable replacement I2S proteins or enzymes are delivered in stable formulations for subcutaneous administration. A desired formulation may facilitate the effective uptake into the circulation, delivery and distribution of an I2S enzyme to targeted tissues, cells and/or organelles of the body. Typically, a suitable formulation for the present invention is a saline based solution.

In some embodiments, formulations for subcutaneous delivery have been formulated such that they are capable of stabilizing, or alternatively slowing or preventing the degradation, of a replacement I2S enzyme. As used herein, the term "stable" refers to the ability of the therapeutic agent (i.e., an I2S enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., preferably for at least 1, 3, 6, 12, 18, 24, 30, 36 months or more). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Stability of the therapeutic agent (i.e., an I2S enzyme) is of particular importance. Stability of the therapeutic agent (i.e., an I2S enzyme) may be further assessed relative to the biological activity or physiochemical integrity of the therapeutic agent over extended periods of time. For example, stability at a given time point may be compared against stability at an earlier time point (e.g., upon formulation day 0) or against unformulated therapeutic agent and the results of this comparison expressed as a percentage. Preferably, the pharmaceutical compositions of the present invention maintain at least 100%, at least 99%, at least 98%, at least 97% at least 95%, at least 90%, at least 85%, at least 80%, at least 75%, at least 70%, at least 65%, at least 60%, at least 55% or at least 50% of the therapeutic agent's biological activity or physiochemical integrity over an extended period of time (e.g., as measured over at least about 6-12 months, at room temperature or under accelerated storage conditions).

Suitable formulations, in either aqueous, pre-lyophilized, lyophilized or reconstituted form, may contain a replacement I2S enzyme at various concentrations. In some embodiments, formulations may contain a replacement I2S enzyme at a concentration in the range of about 0.1 mg/ml to 300 mg/ml (e.g., about 0.1 mg/ml to 250 mg/ml, about 0.1 mg/ml to 200 mg/ml, about 0.1 mg/ml to 150 mg/ml, about 0.1 mg/ml to 100 mg/ml, about 0.1 mg/ml to 80 mg/ml, about 0.1 mg/ml to 60 mg/ml, about 0.1 mg/ml to 50 mg/ml, about 0.1 mg/ml to 40 mg/ml, about 0.1 mg/ml to 30 mg/ml, about 0.1 mg/ml to 25 mg/ml, about 0.1 mg/ml to 20 mg/ml, about 0.1 mg/ml to 60 mg/ml, about 0.1 mg/ml to 50 mg/ml, about 0.1 mg/ml to 40 mg/ml, about 0.1 mg/ml to 30 mg/ml, about 0.1 mg/ml to 25 mg/ml, about 0.1 mg/ml to 20 mg/ml, about 0.1 mg/ml to 15 mg/ml, about 0.1 mg/ml to 10 mg/ml, about 0.1 mg/ml to 5 mg/ml, about 1 mg/ml to 10 mg/ml, about 1 mg/ml to 20 mg/ml, about 1 mg/ml to 40 mg/ml, about 5 mg/ml to 100 mg/ml, about 5 mg/ml to 50 mg/ml, or about 5 mg/ml to 25 mg/ml). In some embodiments, formulations according to the invention may contain a replacement I2S enzyme at a concentration of approximately 1 mg/ml, 5 mg/ml, 10 mg/ml, 15 mg/ml, 20 mg/ml, 25 mg/ml, 30 mg/ml, 40 mg/ml, 50 mg/ml, 60 mg/ml, 70 mg/ml, 80 mg/ml, 90 mg/ml, 100 mg/ml, 150 mg/ml, 160 mg/ml, 170 mg/ml, 180 mg/ml, 190 mg/ml, 200 mg/ml, 300 mg/ml, 400 mg/ml, 500 mg/ml or 600 mg/ml.

In some embodiments, suitable formulations are characterized by their tolerability either as aqueous solutions or as reconstituted lyophilized solutions. As used herein, the terms "tolerable" and "tolerability" refer to the ability of a pharmaceutical composition to not elicit an adverse reaction in the subject to whom such composition is administered, or alternatively not to elicit a serious adverse reaction in the subject to whom such composition is administered.

In some embodiments, suitable formulations for the present invention have desired pH and excipients to maintain their solubility and stability of a replacement I2S protein and to facilitate effective delivery and distribution of a replacement I2S enzyme to blood, targeted tissues, cells and/or organelles of the body.

In some embodiments, suitable formulations for the present invention maintain a pH between about 3.0-8.0 (e.g., about 3.0, 3.5, 4.0, 4.5, 5.0, 5.5, 5.6, 5.7, 5.8, 5.9, 6.0, 6.1, 6.2, 6.3, 6.4, 6.5, 6.6, 6.7, 6.8, 6.9, 7.0, 7.5, or 8.0). In some embodiments, the pH of the formulation is between about 5.0-7.5, between about 5.5-7.0, between about 6.0-7.0, between about 5.5-6.0, between about 5.5-6.5, between about 5.0-6.0, between about 5.0-6.5 and between about 6.0-7.5. Suitable buffers for maintaining desired pH of suitable formulations include, for example acetate, citrate, histidine, phosphate, succinate, tris(hydroxymethyl)aminomethane ("Tris") and other organic acids. In some embodiments, a buffering agent is present in aqueous and/or pre-lyophilized formulations at a concentration ranging between about 1 mM to about 150 mM, or between about 10 mM to about 50 mM, or between about 15 mM to about 50 mM, or between about 20 mM to about 50 mM, or between about 25 mM to about 50 mM. In some embodiments, a suitable buffering agent is present at a concentration of approximately 1 mM, 5 mM, 10 mM, 15 mM, 20 mM, 25 mM, 30 mM, 35 mM, 40 mM, 45 mM, 50 mM, 75 mM, 100 mM, 125 mM or 150 mM.

In some embodiments, suitable formulations contain an isotonicity agent to keep the formulations isotonic. Typically, by "isotonic" is meant that the formulation of interest has essentially the same osmotic pressure as human blood. Isotonic formulations will generally have an osmotic pressure from about 240 mOsm/kg to about 350 mOsm/kg. Isotonicity can be measured using, for example, a vapor pressure or freezing point type osmometers. Exemplary isotonicity agents include, but are not limited to, glycine, sorbitol, mannitol, sodium chloride and arginine. In some embodiments, suitable isotonic agents may be present in aqueous and/or pre-lyophilized formulations at a concentration from about 0.01-5% (e.g., 0.05, 0.1, 0.15, 0.2, 0.3, 0.4, 0.5, 0.6, 0.7, 0.8, 0.9, 1.0, 1.1, 1.2, 1.3, 1.4, 1.5, 2.0, 2.5, 3.0, 4.0 or 5.0%) by weight. In particular embodiments, a suitable formulation for the invention contains sodium chloride at a concentration of about 0.9%.

In some embodiments, it is desirable to add a surfactant to formulations. Exemplary surfactants include nonionic surfactants such as Polysorbates (e.g., Polysorbates 20 or 80); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68, etc.). Typically, the amount of surfactant added is such that it reduces aggregation of the protein and minimizes the formation of particulates or effervescence. For example, a surfactant may be present in a formulation at a concentration from about 0.001-0.5% (e.g., about 0.005-0.05%, or 0.005-0.01%). In particular, a surfactant may be present in a formulation at a concentration of approximately 0.005%, 0.01%, 0.02%, 0.03%, 0.04%, 0.05%, 0.1%, 0.2%, 0.3%, 0.4%, or 0.5%, etc. Alternatively, or in addition, the surfactant may be added to the lyophilized formulation, pre-lyophilized formulation and/or the reconstituted formulation.

In some embodiments, formulations may contain a stabilizing agent, excipient or lyoprotectant, to protect the protein. Typically, a suitable stabilizing agent is a sugar, a non-reducing sugar and/or an amino acid. Exemplary sugars include, but are not limited to, dextran, lactose, mannitol, mannose, sorbitol, raffinose, sucrose and trehalose. Exemplary amino acids include, but are not limited to, arginine, glycine and methionine. Additional stabilizing agents may include sodium chloride, hydroxyethyl starch and polyvinylpyrolidone. Exemplary stabilizing agent concentrations in a suitable formulation may range from about 1 mM to about 400 mM (e.g., from about 30 mM to about 300 mM, and from about 50 mM to about 100 mM), or alternatively, from 0.1% to 15% (e.g., from 1% to 10%, from 5% to 15%, from 5% to 10%) by weight Other pharmaceutically acceptable carriers, excipients or stabilizers such as those described in Remington's Pharmaceutical Sciences 16th edition, Osol, A. Ed. (1980) may be included in the formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include, but are not limited to, additional buffering agents; preservatives; co-solvents; antioxidants including ascorbic acid and methionine; chelating agents such as EDTA; metal complexes (e.g., Zn-protein complexes); biodegradable polymers such as polyesters; and/or salt-forming counter ions such as sodium.

Formulations, in either aqueous, pre-lyophilized, lyophilized or reconstituted form, in accordance with the present invention can be assessed based on product quality analysis, reconstitution time (if lyophilized), quality of reconstitution (if lyophilized), high molecular weight, moisture, and glass transition temperature. Typically, protein quality and product analysis include product degradation rate analysis using methods including, but not limited to, size exclusion HPLC (SE-HPLC), cation exchange-HPLC (CEX-HPLC), X-ray diffraction (XRD), modulated differential scanning calorimetry (mDSC), reversed phase HPLC (RP-HPLC), multi-angle light scattering (MALS), fluorescence, ultraviolet absorption, nephelometry, capillary electrophoresis (CE), SDS-PAGE, and combinations thereof. In some embodiments, evaluation of product in accordance with the present invention may include a step of evaluating appearance (either liquid or cake appearance).

Generally, formulations (lyophilized or aqueous) can be stored for extended periods of time at room temperature. Storage temperature may typically range from 0° C. to 45° C. (e.g., 4° C., 20° C., 25° C., 45° C. etc.). Formulations may be stored for a period of months to a period of years. Storage time generally will be 24 months, 12 months, 6 months, 4.5 months, 3 months, 2 months or 1 month. Formulations can be stored directly in the container used for administration, eliminating transfer steps.

Formulations can be stored directly in the lyophilization container (if lyophilized), which may also function as the reconstitution vessel, eliminating transfer steps. Alternatively, lyophilized product formulations may be measured into smaller increments for storage. Storage should generally avoid circumstances that lead to degradation of the proteins, including but not limited to exposure to sunlight, UV radiation, other forms of electromagnetic radiation, excessive heat or cold, rapid thermal shock, and mechanical shock.

For subcutaneous administration an injection volume in range of approximately 0-10 ml (e.g., approximately 0-5 ml, 0-4 ml, 0-3 ml, 0-2 ml, 0-1 ml, 10 µl to 100 µl, 100 µl to 1 ml, 1 ml to 2 ml, 1 ml to 5 ml, 1 ml to 10 ml) or more may be used. However, the injection volume of fluid in which the I2S administered will typically depend, among other things, on the size of the subject, the dose of the I2S, and the location of subcutaneous administration. Generally, a suitable formulation is formulated such a way that a suitable dosage of a replacement I2S enzyme will be obtained in any given unit dose or single dose form. In some embodiments, a single unit dose is provided in an injection volume of or less than about 5 ml, of or less than about 4.5 ml, of or less than about 4.0 ml, of or less than about 3.5 ml, of or less than about 3.0 ml, of or less than about 2.5 ml, of or less than about 2.0 ml, of or less than about 1.5 ml, of or less than about 1.0 ml, of or less than about 0.8 ml, of or less than about 0.6 ml, of or less than about 0.5 ml.

Biodistribution and Bioavailability

As discussed above, the present invention provides effective delivery of a replacement I2S enzyme to target tissues by subcutaneous administration. As used herein, the term "target tissue" refers to any tissue that is affected by Hunter syndrome or any lysosomal storage disease associated with I2S-deficiency and/or any tissue in which the deficient I2S enzyme is normally expressed. In some embodiments, target tissues include those tissues in which there is a detectable or abnormally high amount of enzyme substrate, for example, GAG, stored in the cellular lysosomes of the tissue, in patients suffering from or susceptible to Hunter syndrome or other lysosomal storage diseases associated with I2S-deficiency. In some embodiments, target tissues include those tissues that display disease-associated pathology, symptom, or feature. Target tissues may include, but are not limited to, blood system, liver, kidney, heart, endothelium, bone marrow and bone marrow derived cells, spleen, lung, lymph node, bone, cartilage, ovary and testis. In various embodiments, subcutaneous administration according to the present invention can deliver a replacement I2S enzyme to one or more target tissues.

In various embodiments, once delivered to target tissue, a replacement I2S enzyme is localized intracellularly. For example, a replacement I2S enzyme may be localized to lysosomes, mitochondria or vacuoles of a target cell.

In some embodiments, a replacement I2S enzyme delivered according to the present invention may achieve therapeutically or clinically effective levels or activities in various targets tissues described herein. As used herein, a therapeutically or clinically effective level or activity is a level or activity sufficient to confer a therapeutic effect in a target tissue. The therapeutic effect may be objective (i.e., measurable by some test or marker) or subjective (i.e., subject gives an indication of or feels an effect). For example, a therapeutically or clinically effective level or activity may be an enzymatic level or activity that is sufficient to ameliorate symptoms associated with the disease in the target tissue (e.g., GAG storage).

In some embodiments, a replacement I2S enzyme delivered according to the present invention may achieve an enzymatic level or activity that is at least 5%, 10%, 20%, 30%, 40%, 50%, 60%, 70%, 80%, 90%, 95% of the normal I2S level or activity in the target tissue. In some embodiments, a replacement I2S enzyme delivered according to the present invention may achieve an enzymatic level or activity that is increased by at least 20%, 40%, 50%, 60%, 80%, 90%, 1-fold, 2-fold, 3-fold, 4-fold, 5-fold, 6-fold, 7-fold, 8-fold, 9-fold or 10-fold as compared to a control (e.g., endogenous levels or activities without the treatment). In some embodiments, a replacement I2S enzyme delivered according to the present invention may achieve an increased enzymatic level or activity at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg in a target tissue.

As discussed in the Examples section, a replacement I2S enzyme delivered subcutaneously according to the present invention can be absorbed into circulation (e.g., serum) effectively and completely and exhibits unexpectedly equal bioavailability as compared to intravenous administration.

In some embodiments, at least 15%, at least 20%, at least 25%, at least 30%, at least 40%, at least 50%, at least 60%, at least 70%, at least 80%, at least 90%, at least 95%, at least 99%, or 100% of the administered dose is absorbed to the blood of a subject within 24 hours, within 36 hours, within 48 hours, within 60 hours, within 72 hours, within 84 hours, within 96 hours, within 108 hours, or within 120 hours following administration to the subject.

In general, a replacement I2S enzyme delivered according to the present invention have a sufficiently long half-life in serum and target tissues and organs. In some embodiments, a replacement I2S enzyme delivered according to the present invention may have a half-life of at least approximately 30 minutes, 45 minutes, 60 minutes, 90 minutes, 2 hours, 3 hours, 4 hours, 5 hours, 6 hours, 7 hours, 8 hours, 9 hours, 10 hours, 12 hours, 16 hours, 18 hours, 20 hours, 24 hours, 30 hours, 36 hours, 42 hours, 48 hours, up to 3 days, up to 7 days, up to 14 days, up to 21 days, or up to a month. In some embodiments, a replacement I2S enzyme delivered according to the present invention may retain detectable level or activity in bloodstream after 12 hours, 24 hours, 30 hours, 36 hours, 42 hours, 48 hours, 54 hours, 60 hours, 66 hours, 72 hours, 78 hours, 84 hours, 90 hours, 96 hours, 102 hours, or a week following administration. Detectable level or activity may be determined using various methods known in the art.

In some embodiments, serum concentration of a replacement I2S enzyme after subcutaneous administration according to the present invention is about 1.0-fold, 1.1-fold, 1.2-fold, 1.3-fold, 1.4-fold, 1.5-fold, 1.6-fold, 1.7-fold, 1.8-fold, 1.9-fold or 2.0-fold higher than that post intravenous administration at 24 hours at the same dose level.

Thus, it is contemplated that increased bioavailability following subcutaneous administration according to the present invention can facilitate efficient delivery of a therapeutically effective amount or dose of a replacement I2S enzyme.

In some embodiments, a suitable therapeutically effective dose ranges from about 0.005 mg/kg body weight to 500 mg/kg body weight, e.g., from about 0.005 mg/kg body weight to 400 mg/kg body weight, from about 0.005 mg/kg body weight to 300 mg/kg body weight, from about 0.005 mg/kg body weight to 200 mg/kg body weight, from about 0.005 mg/kg body weight to 100 mg/kg body weight, from about 0.005 mg/kg body weight to 50 mg/kg body weight, from about 0.005 mg/kg body weight to 25 mg/kg body weight, from about 0.005 mg/kg body weight to 20 mg/kg body weight, from about 0.005 mg/kg body weight to 15 mg/kg body weight, from about 0.005 mg/kg body weight to 10 mg/kg body weight, from about 0.005 mg/kg body weight to 5 mg/kg body weight, from about 0.005 mg/kg body weight to 1 mg/kg body weight, from about 0.05 mg/kg body weight to 10 mg/kg body weight, from about 0.05 mg/kg body weight to 5 mg/kg body weight, from about 0.05 mg/kg body weight to 2.5 mg/kg body weight.

In some embodiments, a therapeutically effective dose is about 0.1 mg/kg body weight or greater, about 0.2 mg/kg body weight or greater, about 0.3 mg/kg body weight or greater, about 0.4 mg/kg body weight or greater, about 0.5 mg/kg body weight or greater, about 0.6 mg/kg body weight or greater, about 0.7 mg/kg body weight or greater, about 0.8 mg/kg body weight or greater, about 0.9 mg/kg body weight or greater, about 1.0 mg/kg body weight or greater, about 1.5 mg/kg body weight or greater, about 2 mg/kg body weight or greater, about 2.5 mg/kg body weight or greater, about 3 mg/kg body weight or greater, about 4 mg/kg body weight or greater, about 5 mg/kg body weight, about 10 mg/kg body weight or greater, about 15 mg/kg body weight or greater, about 20 mg/kg body weight or greater.

In some embodiments, a suitable therapeutically effective dose of a recombinant I2S enzyme is sufficient to achieve serum concentration of the replacement I2S enzyme great than about 1 ng/ml, 5 ng/ml, 10 ng/ml, 20 ng/ml, 25 ng/ml, 50 ng/ml, 75 ng/ml, 100 ng/ml, 200 ng/ml, 300 ng/ml, 400 ng/ml, 500 ng/ml. In some embodiments, a suitable therapeutically effective dose of a recombinant I2S enzyme is an amount sufficient to achieve serum concentration of the replacement I2S enzyme within a range from about 10 ng/ml to 10,000 ng/ml, (e.g., from about 10 ng/ml to 7,500 ng/ml, from about 10 ng/ml to 5,000 ng/ml, from about 10 ng/ml to 2,500 ng/ml, from about 10 ng/ml to 1,000 ng/ml, from about 10 ng/ml to 500 ng/ml, from about 100 ng/ml to 10,000 ng/ml, from about 10 ng/ml to 100 ng/ml, or from about 100 ng/ml to 1000 ng/ml) within 24 hours, within 48 hours, within 72 hours, within 96 hours, or within 120 hours following administration to the subject.

In some embodiments, a suitable therapeutically effective dose of a recombinant I2S enzyme is sufficient to achieve the average maximum serum concentration ($C_{max}$) of the replacement I2S enzyme greater than about 1.0 µg/ml, 1.5 µg/ml, 2.0 µg/ml, 2.5 µg/ml, 5.0 µg/ml, 7.5 µg/ml, 10 µg/ml 1 day, 2 days, 3 days, 1 week, 2 weeks, 3 weeks, 4 weeks, 5 weeks, 10 weeks, 15 weeks, 20 weeks, 25 weeks, 30 weeks, 35 weeks, 40 weeks, 45 weeks, or 50 weeks following administration according to the invention.

In some embodiments, a suitable therapeutically effective dose of a recombinant I2S enzyme is sufficient to achieve the average area under the concentration-time curve (AUC) greater than about 50 min*µg/ml, 75 min*µg/ml, 100 min*µg/ml, 125 min*µg/ml, 150 min*µg/ml, 175 min*µg/ml, 200 min*µg/ml, 225 min*µg/ml, 250 min*µg/ml, 300 min*µg/ml, 350 min*µg/ml, 400 min*µg/ml, 450 min*µg/ml, or 500 mien/mil day, 2 days, 3 days, 1 week, 2 weeks, 3 weeks, 4 weeks, 5 weeks, 10 weeks, 15 weeks, 20 weeks, 25 weeks, 30 weeks, 35 weeks, 40 weeks, 45 weeks, or 50 weeks following administration according to the invention.

Treatment of Hunter Syndrome and Other I2S Deficiency

The present invention may be used to effectively treat individuals suffering from or susceptible to Hunter syndrome or other types of I2S deficiency. The terms, "treat" or "treatment," as used herein, refers to amelioration of one or more symptoms associated with the disease, prevention or delay of the onset of one or more symptoms of the disease, and/or lessening of the severity or frequency of one or more symptoms of the disease.

In some embodiments, treatment refers to decreased lysosomal storage (e.g., of GAG) in various target tissues. In certain embodiments, lysosomal storage is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, lysosomal storage is decreased by at least 1-fold, 2-fold, 3-fold, 4-fold, 5-fold, 6-fold, 7-fold, 8-fold, 9-fold or 10-fold as compared to a control. In some embodiments, lysosomal storage is measured by the presence of lysosomal storage granules (e.g., zebra-striped morphology). The presence of lysosomal storage granules can be measured by various means known in the art, such as by histological analysis.

In some embodiments, treatment refers to increased I2S enzyme level or activity in various target tissues. In some embodiments, I2S enzyme level or activity is increased by about 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900% 1000% or more as compared to a control. In some embodiments, I2S enzyme level or activity is increased by at least 1-fold, 2-fold, 3-fold, 4-fold, 5-fold, 6-fold, 7-fold, 8-fold, 9-fold or 10-fold as compared to a control. In some embodiments, increased I2S enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg, 600 nmol/hr/mg or more. In some embodiments, increased I2S enzymatic level or activity is at least approximately 10%, 15%, 20%, 25%, 30%, 35%, 40%, 45%, 50%, 55%, 60%, 65%, 70%, 75%, 80%, 85%, 90%, 95% of normal I2S enzymatic level or activity.

In some embodiments, treatment refers to reduced size or volume of one or more diseased tissues or organelles, such as liver, or spleen. In some embodiments, treatment according to the present invention results in reduced liver and/or spleen by at least 10%, 20%, 30%, 40%, 50%, 60%, 70%, 80%, 90%, 1-fold, 1.5-fold, or 2-fold by size or volume as compared to a control. Size or volume of tissues or organs may be determined by relative weight/volume, which may be analyzed by, for example, magnetic resonance imaging (MRI) and/or magnetic resonance spectroscopy (MRS). E.g., see d'Assignies et al. *Magnetic Resonance* 21:301 2011, the contents of which are incorporated herein by reference. Additional tissue analysis methods include, but are not limited to, computed tomography (CT), tissue biopsy, biochemical tests of tissue function, ultrasound, Xenon clearance rates, or combinations thereof.

In some embodiments, treatment refers to improved walking capacity in the subject. Various methods can be used to evaluate walking capacity, for example, the 6-Minute Walk Test. In some embodiments, the walking capacity is improved by, on average, at least 10 meters, 15 meters, 20 meters, 25 meters, 30 meters, 35 meters, 40 meters, 45 meters, 50 meters, 55 meters, 60 meters, 65 meters, 70 meters, 75 meters, 80 meters, 85 meters, 90 meters, 95 meters, 100 meters, 110 meters, 120 meters, 130 meters, 140 meters, 150 meters, 160 meters, 170 meters, 180 meters, 190 meters, 200 meters, 210 meters, 220 meters, 230 meters, 240 meters, 250 meters, or more as determined by the 6-Minute Walk Test as compared to a control. In some embodiments, the walking capacity is improved by, on average, 10%, 20%, 30%, 40%, 50%, 60%, 70%, 80%, 90%, 1-fold, 2-fold, 3-fold, 4-fold, 5-fold, 6-fold, 7-fold, 8-fold, 9-fold, 10-fold, or more as determined by the 6-Minute Walk Test as compared to a control.

In some embodiments, treatment refers to increased survival (e.g. survival time). For example, treatment can result in an increased life expectancy of a patient. In some embodiments, treatment according to the present invention results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with similar disease without treatment. In some embodiments, treatment according to the present invention results in an increased life expectancy of a patient by more than about 6 month, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with similar disease without treatment. In some embodiments, treatment according to the present invention results in long term survival of a patient. As used herein, the term "long term survival" refers to a survival time or life expectancy longer than about 40 years, 45 years, 50 years, 55 years, 60 years, or longer.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with Hunter syndrome, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having Hunter syndrome or having the potential to develop Hunter syndrome. The individual can have residual endogenous I2S expression and/or activity, or no measurable activity. For example, the individual having Hunter syndrome may have I2S expression levels that are less than about 30-50%, less than about 25-30%, less than about 20-25%, less than about 15-20%, less than about 10-15%, less than about 5-10%, less than about 0.1-5% of normal I2S expression levels.

Immune Tolerance

Generally, subcutaneous administration of a replacement enzyme according to the present invention does not result in severe adverse effects in the subject. As used herein, severe adverse effects induce, but are not limited to, substantial immune response, toxicity, or death. As used herein, the term "substantial immune response" refers to severe or serious immune responses, such as adaptive T-cell immune responses.

Thus, in many embodiments, inventive methods according to the present invention do not involve concurrent immunosuppressant therapy (i.e., any immunosuppressant therapy used as pre-treatment/pre-conditioning or in parallel to the method). In some embodiments, inventive methods according to the present invention do not involve an immune tolerance induction in the subject being treated. In some embodiments, inventive methods according to the present invention do not involve a pre-treatment or preconditioning of the subject using T-cell immunosuppressive agent.

In some embodiments, subcutaneous administration of a replacement enzyme can mount an immune response against these agents. Thus, in some embodiments, it may be useful to render the subject receiving the replacement enzyme tolerant to the enzyme replacement therapy. Immune tolerance may be induced using various methods known in the art.

Any immunosuppressant agent known to the skilled artisan may be employed together with a combination therapy of the invention. Such immunosuppressant agents include but are not limited to cyclosporine, FK506, rapamycin, CTLA4-Ig, and anti-TNF agents such as etanercept (see e.g. Moder, 2000, Ann. Allergy Asthma Immunol. 84, 280-284; Nevins, 2000, Curr. Opin. Pediatr. 12, 146-150; Kurlberg et al., 2000, Scand. J. Immunol. 51, 224-230; Ideguchi et al., 2000, Neuroscience 95, 217-226; Potter et al., 1999, Ann. N.Y. Acad. Sci. 875, 159-174; Slavik et al., 1999, Immunol. Res. 19, 1-24; Gaziev et al., 1999, Bone Marrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The anti-IL2 receptor (.alpha.-subunit) antibody daclizumab (e.g. Zenapax™), which has been demonstrated effective in transplant patients, can also be used as an immunosuppressant agent (see e.g. Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1127-1137; Eckhoff et al., 2000, Transplantation 69, 1867-1872; Ekberg et al., 2000, Transpl. Int. 13, 151-159). Additionalimmunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin. Nephrol. 20, 108-125; Chirmule et al., 2000, J. Virol. 74, 3345-3352; Ito et al., 2000, J. Immunol. 164, 1230-1235).

Administration

Inventive methods of the present invention contemplate single as well as multiple subcutaneous administrations of a therapeutically effective dose of a replacement enzyme described herein. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region.

Replacement enzymes can be administered at regular intervals, depending on the nature, severity and extent of the subject's condition. In some embodiments, a therapeutically effective dose of a replacement enzyme may be administered subcutaneously periodically at regular intervals (e.g., once every year, once every six months, once every five months, once every three months, bimonthly (once every two months), monthly (once every month), biweekly (once every two weeks), weekly, daily or at variable intervals).

In some embodiments, subcutaneous administration may be used in conjunction with other routes of administration (e.g., intravenous, intrathecally, intramuscularly, transdermally, or transmucosally (e.g., orally or nasally)). In some embodiments, those other routes of administration (e.g., intravenous or intrathecal administration) may be performed no more frequent than biweekly, monthly, once every two months, once every three months, once every four months, once every five months, once every six months, annually administration. In certain embodiments, those other routes of administration (e.g., intravenous or intrathecal administration) is performed more frequent than monthly administration, such as twice weekly, weekly, every other week, or twice monthly. In some embodiments, subcutaneous and intravenous or intrathecal administrations are performed on the same day. In some embodiments, subcutaneous and intravenous or intrathecal administrations are not performed within a certain amount of time of each other, such as not within at least 2 days, within at least 3 days, within at least 4 days, within at least 5 days, within at least 6 days, within at least 7 days, or within at least one week. In some embodiments, subcutaneous and intravenous or intrathecal administrations are performed on an alternating schedule, such as alternating administrations weekly, every other week, twice monthly, or monthly. In some embodiments, an subcutaneous administration replaces an intravenous or intrathecal administration in an administration schedule, such as in a schedule of intravenous or intrathecal administration weekly, every other week, twice monthly, or monthly, every third or fourth or fifth administration in that schedule can be replaced with a subcutaneous administration in place of an intravenous or intrathecal administration. In some embodiments, subcutaneous and intravenous or intrathecal administrations are performed sequentially, such as performing subcutaneous administrations first (e.g., weekly, every other week, twice monthly, or monthly dosing for two weeks, a month, two months, three months, four months, five months, six months, a year or more) followed by intravenous or intrathecal administrations (e.g., weekly, every other week, twice monthly, or monthly dosing for more than two weeks, a month, two months, three months, four months, five months, six months, a year or more). In some embodiments, intravenous or intrathecal administrations are performed first (e.g., weekly, every other week, twice monthly, monthly, once every two months, once every three months dosing for two weeks, a month, two months, three months, four months, five months, six months, a year or more) followed by subcutaneous administrations (e.g., weekly, every other week, twice monthly, or monthly dosing for more than two weeks, a month, two months, three months, four months, five months, six months, a year or more).

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect, such as an amount sufficient to modulate lysosomal enzyme receptors or their activity to thereby treat such lysosomal storage disease or the symptoms thereof (e.g., a reduction in or elimination of the presence or incidence of "zebra bodies" or cellular vacuolization following the administration of the compositions of the present invention to a subject). Generally, the amount of a therapeutic agent (e.g., a recombinant lysosomal enzyme) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Kits

The present invention further provides kits or other articles of manufacture which contains a replacement I2S enzyme or a formulation containing the same and provides instructions for its reconstitution (if lyophilized) and/or use. Kits or other articles of manufacture may include a container, a syringe, vial and any other articles, devices or equipment useful in subcutaneous administration. Suitable containers include, for example, bottles, vials, syringes (e.g., pre-filled syringes), ampules, cartridges, reservoirs, or lyojects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may hold formulations and a label on, or associated with, the container that may indicate directions for reconstitution and/or use. For example, the label may indicate that the formulation is reconstituted to protein concentrations as described above. The label may further indicate that the formulation is useful or intended for, for example, subcutaneous administration. In some embodiments, a container may contain a single dose of a stable formulation containing a replacement enzyme. In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 25 mg/ml, at least 50 mg/ml, at least 75 mg/ml, at least 100 mg/ml). Kits or other articles of manufacture may further include other materials desirable from a commercial and user standpoint, including other buffers, diluents, filters, needles, syringes, and package inserts with instructions for use. In some embodiments, kits or other articles of manufacture may include an instruction for elf-administration.

The invention will be more fully understood by reference to the following examples. They should not, however, be construed as limiting the scope of the invention. All literature citations are incorporated by reference.

EXAMPLES

Example 1

IV and Subcutaneous (SC) Administration of Recombinant Iduronate 2-Sulfatase in Non-Human Primates (NHPs)

The purpose of the present example, was to perform a study to evaluate subcutaneous (SC) administration of a recombinant form of iduronate-2-sulfatase (rI2S). As part of the evaluation, bioavailability and other pharmacokinetic parameters were empirically determined following SC administration, in order to assess the overall effectiveness of the treatment in non-human primates.

In the current study, SC administration of rI2S was investigated to evaluate the efficacy of the approach, as compared to the traditional IV approach. As a result, one additional goal of the current study, is to use elucidate if subcutaneous administration is an equally effective route of administration; and using the data obtained from NHPs to extrapolate and predict conditions for SC administration in humans in order to design an effective therapeutic regimen.

Overview of the Experimental Model System and Experimental Treatments

For the study, two groups of three non-human primates (NHPs) were selected for evaluating the effectiveness of subcutaneous treatment of recombinant iduronate-2-sulfatase (rI2S) as compared to IV administration. Group one (Table 2), consisted of three non-naïve male Cynomolgus monkeys, treated weekly over the course of five weeks and subjected to Treatments 1 through 4. Group two (Table 2), consisted of three non-naïve male Cynomolgus monkeys, treated weekly over the course of two weeks and subjected only to Treatments 5. Cynomolgus monkeys within both group 1 and 2 were approximately 2 years in age and had been used in previously unrelated studies. The body weights of the three monkeys in group 1 at the beginning of the study were 2.8 (Monkey 5305), 2.4 (Monkey 5306) and 2.5 (Monkey 5324) (2.6±0.2, mean±SD, n=3) kilograms (see Table 2). The body weights of the three monkeys in group 2 at the beginning of the study were 4.3 (Monkey 5265), 3.5 (Monkey 5319) and 3.4 (Monkey 5363) (3.7±0.5, mean±SD, n=3) kilograms, respectively (see Table 2).

Each treatment of single administration was followed by a one-week period of washout time. For the purpose of the experiment, intravenous (IV) administration (Treatment 1) was designed to serve as a reference control, representing a theoretical bioavailability of (100%). Intravenous rI2S was administered at a dose of 0.5 mg/kg (Table 3). The remaining Treatments 2-5 were all administered subcutaneously and varied according to concentrations and injections location (Table 3).

TABLE 2

Experimental Groups

| Experimental Group | Animal Ref. No. | Initial Body Weight (kg) | Experimental Treatment |
|---|---|---|---|
| 1 | 5305 | 2.8 | 1, 2, 3, 4 |
|   | 5306 | 2.4 | 1, 2, 3, 4 |
|   | 5324 | 2.5 | 1, 2, 3, 4 |
| 2 | 5265 | 4.3 | 5 |
|   | 5319 | 3.5 | 5 |
|   | 5363 | 3.4 | 5 |

TABLE 3

Dosing routes, doses, volumes, locations, time in each of five treatments

| Experimental Group | Treatment (group) | Route | Dose mg/kg | Dosing Volume mL/ dosing | Dosing Area Location | ~Dosing time (day) from Initiation |
|---|---|---|---|---|---|---|
| 1 | 1 | IV | 0.5 | 1 | IV | 0 |
|   | 2 | SC | 2.5 | 1 | scapular | 7 |
|   | 3 | SC | 10 | 1 | scapular | 14 |
|   | 4 | SC | 2.5 | 5 | thigh | 21 |
| 2 | 5 | SC | 1.0 | 1 | thigh | 0 |

Testing for Immunogenic Status

As part of the evaluation for treating a NHPs with rI2S, antigenic tolerance for the rI2S protein was examined. Blood samples were collected prior to the start of each of Treatments 1-4 for determining a baseline reading for the immunogenic status against the dosed rI2S protein. For experimental Treatment 1, following IV administration twelve blood samples were collected at predetermined intervals over a 24 hour period. For subcutaneous treatment, a total of thirteen blood samples were collected at predetermined intervals over a 48 hour period for Treatments 2, 3, and 4. Serum samples for the NHPs in group 2 (experimental Treatment 5) were not tested for anti-I2S antibodies because three different animals were only used for a short 2 week period of time. Serum concentrations of rI2S were analysed using an I2S-specific ELISA method, while anti-I2S antibodies in the serum were evaluated using a MSD (MesoScale Discovery) ELISA technique. Samples were deemed to be positive with a cut-off point of 98.4 (MesoScale Discovery signal). The results are summarized in Table 4.

Anti-I2S antibodies were not detected prior to Treatment 1 and 2 in any of three monkeys of group 1. Anti-I2S antibodies were observed at a low concentration (35 ng/mL) in Monkey 5324 (group 1) prior to the start of experimental Treatment 3. However, rI2S concentrations were still measurable in serum, at all time points after dosing in this animal, due to low titer (640 ng/ml) of the antibodies. Antibodies were also detected in Monkey 5306 (concentration 0.18 ng/mL) and 5324 (417.0 ng/mL), prior to the start of experimental Treatment 4. However, it was only in Monkey 5324 (with a greater concentration of antibodies) that serum rI2S concentrations were not detectable at some time points in Treatment 4. Because only low concentrations of antibodies were detectable in Monkey 5306, PK parameters based on rI2S serum concentration could still be determined

TABLE 4

Results of anti-Elaprase antibody assay

| Treatment | Monkey | MSD* | Concentration ng/mL | Titer |
|---|---|---|---|---|
| 1 | 5305 | 92 | 0.02 | NA |
| 1 | 5306 | 95 | 0.03 | NA |
| 1 | 5324 | 85 | 0.00 | NA |
| 2 | 5305 | 83 | 0.00 | NA |
| 2 | 5306 | 87 | 0.00 | NA |
| 2 | 5324 | 92 | 0.02 | NA |
| 3 | 5305 | 85 | 0.00 | NA |
| 3 | 5306 | 92 | 0.01 | NA |
| 3 | 5324 | 3936 | 35.17 | 640 |

TABLE 4-continued

Results of anti-Elaprase antibody assay

| Treatment | Monkey | MSD* | Concentration ng/mL | Titer |
|---|---|---|---|---|
| 4 | 5305 | 94 | 0.03 | NA |
| 4 | 5306 | 113 | 0.18 | No Data |
| 4 | 5324 | 43073 | 417.00 | 102400 |

*If a MSD signal was greater than 98.4, the sample was considered to be positive for anti-I2S antibodies.

Replacement Enzyme

For the study, two lots (Lots A and B) of an enzymatically active recombinant humanized version of Iduronate-2-sulfatase were used. Lot A was used for Treatments 1 through 4, while Lot B was used for Treatment 5. Recombinant I2S was stably formulated in a solution of 20 mM sodium phosphate, 137 mM sodium chloride at pH 6.0.

Concentration of rI2S in each dose formulation was analyzed using a qualified spectrophotometric method involving Absorbance at a wavelength of 280 nm. Recombinant I2S concentrations in dosing formulations were expressed as ng/ml of serum. Variations between the nominal and actual concentration of rI2S in dosing solutions are summarized in Table 5.

TABLE 5

Comparison of nominal and actual concentrations of rI2S in dosing formulation

| Treatment | Monkey ID | Body weight kg | Nominal mg/mL | Actual mg/mL | Actual/nominal % |
|---|---|---|---|---|---|
| 1 | 5305 | 2.8 | 1.39 | 1.69 | 122 |
| 1 | 5306 | 2.4 | 1.22 | 1.76 | 144 |
| 1 | 5324 | 2.5 | 1.25 | 1.58 | 126 |
| 2 | 5305 | 2.8 | 6.93 | 7.93 | 114 |
| 2 | 5306 | 2.5 | 6.34 | 6.83 | 108 |
| 2 | 5324 | 2.5 | 6.18 | 7.05 | 114 |
| 3 | 5305 | 2.7 | 27.1 | 31.23 | 115 |
| 3 | 5306 | 2.5 | 24.7 | 26.76 | 108 |
| 3 | 5324 | 2.3 | 22.8 | 23.91 | 105 |
| 4 | 5305 | 2.7 | 1.34 | 1.48 | 110 |
| 4 | 5306 | 2.6 | 1.28 | 1.40 | 109 |
| 4 | 5324 | 2.4 | 1.2 | 1.31 | 109 |
| 5 | 5265 | 4.3 | 4.33 | 4.47 | 103.3 |
| 5 | 5319 | 3.5 | 3.48 | 3.14 | 90.1 |
| 5 | 5363 | 3.4 | 3.35 | 3.63 | 108.4 |

Experimental Treatment and Dosing Procedure

Treatment 1—IV Injection in Group 1 (Reference for SC Bioavailability)

Treatment 1 consisted of IV administration of the rI2S protein to NHPs in group 1. During IV administration, protein is injected directly into the circulating blood supply of the body and should theoretically represent complete absorption of the dosed protein into the central compartment. Therefore, for the current study, Treatment 1 was designed to serve as a reference control for each of the different subcutaneous treatments 2-5, representing a theoretical bioavailability of 100%.

Each NHP within group 1 received a 1 mL bolus IV injection of 0.5 mg/kg of rI2S. Blood samples (approximately 0.7 mL/time point) were collected immediately prior to IV injection (Time 0), and for additional predetermined time intervals for the 24 hour period thereafter. An extra volume (0.7 mL) of blood was also sampled at Time 0 for testing the baseline of anti-I2S antibodies. A dosing-free period of 7-days was allowed for animals to eliminate the administered compound from their body prior to the start of the next treatment.

Treatments 2, 3, 4 and 5 (SC Injections for Establishing Bioavailability in NHPs)

For experimental Treatments 2 and 3, rI2S AF was delivered by SC administration at two dose levels in 1 mL injection volume (2.5 mg/kg in Treatment 2, and 10.0 mg/kg in Treatment 3) into the scapular region of each monkey within group 1. Treatment 4 consisted of SC administration at a dose level of 2.5 mg/kg in an injection volume of 5 mL per animal, which was administered into the thigh region of each NHP of group 1. For experimental Treatment 5, each NHP within group 2 received a 1 mL SC injection of rI2S at a dose of 1.0 mg/kg in their thigh area.

Blood samples were collected immediately prior to SC injection (Time 0), and for additional predetermined time intervals for the 48 hour (Treatments 2, 3, and 4) or 96 hour (Treatment 5) period thereafter. Blood was also sampled prior to each of these treatments for determining the status of immunogenicity. A dosing-free period of 7-days was allowed for animals to eliminate the administered compound from the body prior to the start of each experimental treatment.

Pharmacokinetic and Pharmacodynamic Analysis

Serum was processed and collected from the blood samples obtained during each experimental treatment, and stored frozen at −65 to −85° C. until analysis. Serum concentration of I2S was analysed using an I2S-specific ELISA and expressed in ng/mL of serum. The validated low limit of quantification of the ELISA technique was 62.5 ng/mL. Group means for I2S concentrations in serum over time after IV or SC administration are shown in FIG. 1.

Individual serum concentration-time data were analysed using well established non-compartmental models (Model 201 for IV dosing, and Model 200 for SC administrations, WinNonlin version 5.2, PharSight, Mountain View, Calif.) to determine pharmacokinetic (PK) parameters for I2S administration.

AUC (Area under the Concentration Time Curve) values were calculated using standard methods. For example, the following formula can be used to calculate $AUC_{(0-t)}$:

$$AUC_{(0-t)} = \Sigma (t_{i+1} - t_i)/2 \times (C_i + C_{i+1})$$

the summation is from time t=0 to n−1, where n is the number of data points.

In addition, $AUC_{inf}$ can be calculated based on area under the concentration time curve with the last concentration extrapolated based on the elimination rate constant Kel:

$$AUC_{inf} = AUC_{(0-t)} + (C_n/\text{Kel})$$

Elimination rate constant Kel can be calculated using the following formula:

$$\lambda_z = -\ln(10) \times s$$

where s is the slope between the chosen start and end points.

Through standard manipulation and mathematical rearrangement of the equations above, several pharmacokinetic parameters were calculated for each experimental treatment. The pharmacokinetic parameters derived were as follows: Maximum observed serum concentration ($C_{max}$, ng/mL); Time of $C_{max}$ appearance in the serum ($T_{max}$, hours); Area under the serum concentration-time curve from time zero to 24 hours post dose ($AUC_{0-24\ hour}$, hr.ng/mL); area under the serum concentration-time curve from time zero to the last sampling time at which serum concentrations were measurable ($AUC_{last}$, hr.ng/mL); Area under the serum concentration-time curve extrapolated to infinity (AUC$_{inf}$, hr.ng/mL); Apparent terminal rate constant ($\lambda_z$) derived from the slope of the serum concentration-time curve; Terminal half-life ($t_{1/2}$, hours) calculated as $0.693/\lambda_z$; Total clearance (CL, mL/hr/kg) calculated as dose/AUC$_{inf}$; Apparent volume of distribution (V$_z$, mL/kg) based on the terminal phase of concentration-time curve for IV dosing. Volume for SC dosing is actually volume/F, where F is the fraction of dose absorbed; and Bioavailability (F) calculated as AUC$_{inf(SC)}$/AUC$_{inf(IV)}$*100%, based on AUC$_{inf}$ values that was normalized for dose.

Pharmacodynamic (PD) parameters were determined by measuring changes in enzymatic activity over time. Enzyme activity assays were carried out for each of the samples collected over the 48 or 96 hour treatment period, as described above. In brief, enzyme activity within the sample was determined using a substrate specific cleavage assay using 4-MUF for the Iduronate Sulfatase enzyme. The pharmacokinetic parameters calculated were as follows: $C_{max}$, $T_{max}$, $t_{1/2}$, CL/F, V$_z$/F, AUC0-24 $_{hr}$, AUC$_{last}$, and AUC$_{inf}$ PK Analysis of Treatment 1: IV Dosing 0.5 mg/Kg of rI2S in 1 mL Volume Initial serum concentrations of I2S were greater than the lower limit of quantification (62.5 ng/mL) in two of three animals prior to any treatment (Time 0, 86 and 83 ng/mL in Monkeys 5305 and 5306, respectively). Following IV dosing 0.5 mg/kg of rI2S, the distribution phase lasted about 6 hours, which was followed by a terminal elimination phase. The serum concentration was 689±82 ng/mL at 6 hours post dosing, which was approximately 5% of the peak concentration (689/12760=5.4%). Serum concentrations were measurable 24 hours (the last sampling time point in the group) in all three animals (191±34 ng/mL), with a final concentration of approximately 1.5% of the peak concentration (191/12760=1.5%).

PK analysis on the concentration-time data indicated that $C_{max}$ was 12,760±2,449 ng/mL (mean±SD, n=3), resulting in an AUC$_{24hr}$ and AUC$_{inf}$ of approximately 22267±3775 and 25140±3881 hr.ng/mL, respectively. The rate of clearance was 20±3 mL/hr/kg with a terminal half-life of 10.3±1.3 hours. The calculated distribution volume (Vz), based on the empirically determined terminal phase, was 301±66 mL/kg.

TABLE 6

I2S Serum Concentrations for Treatment 1: 0.5 mg/kg, 1 mL IV, n = 3

| Animal ID Time (hour) | 5305 | 5306 | 5324 | Mean ng/mL | SD ng/mL | N |
|---|---|---|---|---|---|---|
| | Concentration (ng/mL) | | | | | |
| 0 | 86 | 83 | 0 | 56 | 49 | 3 |
| 0.08 | 14600 | 9980 | 13700 | 12760 | 2449 | 3 |
| 0.25 | 12100 | 7740 | 10600 | 10147 | 2215 | 3 |
| 0.5 | 8360 | 6220 | 8320 | 7633 | 1224 | 3 |
| 1 | 5350 | 3480 | 4770 | 4533 | 957 | 3 |
| 2 | 2840 | 1540 | 1770 | 2050 | 694 | 3 |
| 3 | 1450 | 1120 | 1360 | 1310 | 171 | 3 |
| 4 | 1260 | 956 | 1030 | 1082 | 159 | 3 |

TABLE 6-continued

I2S Serum Concentrations for Treatment 1: 0.5 mg/kg, 1 mL IV, n = 3

| Animal ID Time (hour) | 5305 | 5306 | 5324 | Mean ng/mL | SD ng/mL | N |
|---|---|---|---|---|---|---|
| | Concentration (ng/mL) | | | | | |
| 6 | 783 | 638 | 652 | 691 | 80 | 3 |
| 8 | 651 | 538 | 528 | 572 | 68 | 3 |
| 10 | 520 | 381 | 385 | 429 | 79 | 3 |
| 24 | 217 | 203 | 153 | 191 | 34 | 3 |

TABLE 7

PK Analysis for Treatment 1: 0.5 mg/kg, 1 mL/animal, IV dosing

| PK Parameter | unit | G1-5305 | G1-5306 | G1-5324 | Mean | SD | N |
|---|---|---|---|---|---|---|---|
| $t_{1/2}$ | hr | 10.4 | 11.5 | 8.9 | 10.3 | 1.3 | 3 |
| $C_{max}$ | ng/mL | 14600 | 9980 | 13700 | 12760 | 2449 | 3 |
| AUC$_{0-24\ hr}$ | hr*ng/mL | 26244 | 18734 | 21822 | 22267 | 3775 | 3 |
| AUC$_{inf}$ | hr*ng/mL | 29514 | 22109 | 23796 | 25140 | 3881 | 3 |
| AUC % $_{extrap}$ | % | 11 | 15 | 8 | 12 | 4 | 3 |
| Vz | mL/kg | 255 | 376 | 271 | 301 | 66 | 3 |
| CL | mL/hr/kg | 16.9 | 22.6 | 21.0 | 20 | 3 | 3 |

PK Analysis of Treatment 2: 2.5 mg/Kg of rI2S (1 mL Volume) by SC Injection into Scapular Area Serum concentrations of I2S were greater than the lower limit of quantification (62.5 ng/mL) in one of three animals prior to Treatment 2 (74.3 ng/mL in Monkey 5305). Following SC administration of 2.5 mg/kg of rI2S, the absorption phase for the protein lasted about 3 hours, and was followed by a terminal elimination phase. A peak protein concentration (2457±2100 ng/mL) was observed at approximately 10.3±11.8 hours after SC dosing, followed by an approximately 50% reduction in serum concentration (1130±72 ng/mL) 24 hours post dosing. Serum concentrations were 499±71 ng/mL at 48 hours (the last sampling time point in this group), which was approximately 20% of the observed peak concentration (499/2457×100%=20%).

PK analysis on the concentration-time data indicated that $C_{max}$ was 2457±2100 ng/mL (mean±SD, n=3) resulting in an AUC$_{24hr}$ and AUC$_{inf}$ of approximately 31062±19150 (n=3) and 82770±3125 hr.ng/mL (n=2), respectively. The rate of clearance was 30±1 mL/hr/kg (n=2) with a terminal half-life of 35.5±20.7 hours (n=2). The calculated distribution volume (V$_z$/F), based on the empirically determined terminal phase, was 1564±960 mL.

In comparison with those after IV dosing in Treatment 1, SC bioavailability in Treatment 2 was 65.8%, based on the values of AUC$_{inf}$ that had been normalized for dose (see Table 9). The value of $C_{max}$ post SC dosing was 3.9% of that post IV dosing. However, the value of rI2S concentration at 24 hours post SC dosing was about 6-fold higher than that observed post IV dosing (1.2-fold higher when the values of concentrations were normalized for dose). The percentage of AUC extrapolated from last time point to infinity was 31±24% of the AUC$_{inf}$.

TABLE 8

I2S Serum Concentrations for Treatment 2: 2.5 mg/kg, 1 mL SC (scapular), n = 3

| Animal ID Time | 5305 | 5306 | 5324 | Mean ng/mL | SD ng/m | N |
|---|---|---|---|---|---|---|
| | Concentration (ng/mL) | | | | | |
| 0 | 74.3 | <LLO | <LLO | 25 | 43 | 3 |
| 0.08 | 75.9 | 109 | | 92 | 23 | 2 |

TABLE 8-continued

I2S Serum Concentrations for Treatment 2: 2.5 mg/kg, 1 mL SC (scapular), n = 3

| Animal ID Time | 5305 | 5306 Concentration (ng/mL) | 5324 | Mean ng/mL | SD ng/m | N |
|---|---|---|---|---|---|---|
| 0.25 | 72.6 | 407 | 107 | 196 | 184 | 3 |
| 0.5 | 142 | 1100 | 333 | 525 | 507 | 3 |
| 0.75 | 233 | 1860 | 463 | 852 | 880 | 3 |
| 1 | 417 | 2720 | 590 | 1242 | 1283 | 3 |
| 2 | 582 | 4640 | 1110 | 2111 | 2206 | 3 |
| 3 | 775 | 4870 | 1320 | 2322 | 2224 | 3 |
| 4 | 816 | 4640 | 1450 | 2302 | 2049 | 3 |
| 8 | 951 | 2980 | 921 | 1617 | 1180 | 3 |
| 12 | 586 | 1300 | 534 | 807 | 428 | 3 |
| 24 | 1050 | 1190 | 1150 | 1130 | 72 | 3 |
| 48 | 543 | 418 | 537 | 499 | 71 | 3 |

<LLOQ: lower than the limit of quantitation

TABLE 9

PK Analysis for Treatment 2: 2.5 mg/kg, 1 mL/animal, SC dosing into scapular area

| PK Parameter | unit | G2-5305 | G2-5306 | G2-5324 | mean | SD | N |
|---|---|---|---|---|---|---|---|
| $t_{1/2}$ | hr | missing | 20.9 | 50.1 | 35.5 | 20.7 | 2 |
| $T_{max}$ | hr | 24.0 | 3.0 | 4.0 | 10.3 | 11.8 | 3 |
| $C_{max}$ | ng/mL | 1050 | 4870 | 1450 | 2457 | 2100 | 3 |
| $AUC_{0-24\ hr}$ | hr*ng/mL | 18571 | 53109 | 21506 | 31062 | 19150 | 3 |
| $AUC_{inf}$ | hr*ng/mL | missing | 84979 | 80560 | 82770 | 3125 | 2 |
| AUC % $_{extrap}$ | % | missing | 15 | 48 | 31 | 24 | 2 |
| Vz | mL/kg | missing | 885 | 2243 | 1564 | 960 | 2 |
| CL | mL/hr/kg | missing | 29 | 31 | 30 | 1 | 2 |

PK Analysis for Treatment 3: 10 mg/Kg of rI2S (1 mL Volume) by SC Injection into Scapular Area Serum concentrations of I2S greater than the lower limit of quantification (62.5 ng/mL) were observed in two of three animals prior to the start of Treatment 3 (80 and 81 ng/mL in Monkeys 5305 and 5306, respectively). Following SC administration of 10 mg/kg of rI2S, the absorption phase lasted approximately 3 hours and was followed by a terminal elimination phase. Peak concentration (8927±4191 ng/mL) was observed at approximately 4.7±3.1 hours after SC dosing. Similar to Treatment 2, an approximately 50% reduction in peak serum concentration (4,550±1,395 ng/mL) 24 hours post dosing. A serum concentration of 1997±394 ng/mL at 48 hours (the last sampling time point in this group) was observed, representing approximately 22% of the peak concentration (see Table 10).

Non-compartmental PK parameters were obtained from all three animals after Treatment 3. The values calculated for $AUC_{0-24\ hour}$ and $AUC_{inf}$ were 143291±74919 and 316435±71338 hr.ng/mL, respectively. The rate of clearance (CL/F) was 33±8 mL/min/kg with a terminal half-life of approximately 31.3±17.3 hours. The calculated distribution volume ($V_z/F$), based on the empirically determined terminal phase, was approximately 1481±772 mL/kg (see Table 11).

Compared with those after IV dosing in Treatment 1, SC bioavailability in Treatment 3 was 62.9%, based on the values of $AUC_{inf}$ that had been normalized for dose (see Table 11). The value of $C_{max}$ post SC dosing was 3.5% of that post IV dosing. However, the value of rI2S concentration at 24 hours post SC dosing was about 24-fold higher than that post IV dosing (1.2-fold higher when the values of concentrations were normalized for dose). The percentage of AUC extrapolated from last time point to infinity was 30±19% of the $AUC_{inf}$.

These data suggest that SC injection at both the 2.5 mg/kg (Treatment 2) and 10.0 mg/kg (Treatment 3) doses into the scapula region, resulted in a higher bioavailability and serum concentration as compared to IV administration. At previously stated, given that IV administration results in delivery of the I2S protein directly into the blood supply, it should result in rapid systemic distribution through the body. In accordance with standard practice, the inventors used IV administration (Treatment 1) as a reference control, representing the maximum possible distribution and a theoretical bioavailability of 100%. In the terms of longer half-life and larger distribution volume, it was further suggested, that SC administration may represent a more effective way to distribute I2S throughout the body.

TABLE 10

Serum I2S Concentration for Treatment 3: 10 mg/kg, 1 mL SC (scapular), n = 3

| Animal ID Time (hour) | 5305 | 5306 Concentration (ng/mL) | 5324 | Mean ng/mL | SD ng/mL | N |
|---|---|---|---|---|---|---|
| 0 | 80 | 81 | <LLOQ | 54 | 46 | 3 |
| 0.08 | 90.2 | 141 | 101 | 111 | 27 | 3 |
| 0.25 | 100 | 495 | 1530 | 708 | 738 | 3 |
| 0.5 | 222 | 1690 | 2550 | 1487 | 1177 | 3 |

TABLE 10-continued

Serum I2S Concentration for Treatment 3: 10 mg/kg, 1 mL SC (scapular), n = 3

| Animal ID | 5305 | 5306 | 5324 | Mean | SD | |
|---|---|---|---|---|---|---|
| Time (hour) | Concentration (ng/mL) | | | ng/mL | ng/mL | N |
| 0.75 | 602 | 2980 | 3790 | 2457 | 1657 | 3 |
| 1 | 1040 | 5180 | 4870 | 3697 | 2306 | 3 |
| 2 | 3700 | 11000 | 7680 | 7460 | 3655 | 3 |
| 3 | 4560 | 12900 | 7480 | 8313 | 4232 | 3 |
| 4 | 5500 | 13200 | 7440 | 8713 | 4005 | 3 |
| 8 | 4450 | 13600 | 5700 | 7917 | 4961 | 3 |
| 12 | 2770 | 9670 | 3800 | 5413 | 3722 | 3 |
| 24 | 4520 | 5960 | 3170 | 4550 | 1395 | 3 |
| 48 | 2400 | 1970 | 1620 | 1997 | 391 | 3 |

TABLE 11

PK Analysis for Treatment 3: 10 mg/kg, 1 mL/animal, SC dosing into scapular area

| PK Parameter | unit | G3-5305 | G3-5306 | G3-5324 | mean | SD | N |
|---|---|---|---|---|---|---|---|
| $t_{1/2}$ | hr | 49.9 | 15.6 | 28.5 | 31.3 | 17.3 | 3 |
| $T_{max}$ | hr | 4.0 | 8.0 | 2.0 | 4.7 | 3.1 | 3 |
| $C_{max}$ | ng/mL | 5500 | 13600 | 7680 | 8927 | 4191 | 3 |
| $AUC_{0-24\ hr}$ | hr*ng/mL | 89981 | 228950 | 110943 | 143291 | 74919 | 3 |
| $AUC_{inf}$ | hr*ng/mL | 345793 | 368409 | 235102 | 316435 | 71338 | 3 |
| $AUC\ \%_{extrap}$ | % | 50 | 12 | 28 | 30 | 19 | 3 |
| Vz | mL/kg | 2082 | 610 | 1751 | 1481 | 772 | 3 |
| CL | mL/hr/kg | 29 | 27 | 43 | 33 | 8 | 3 |

PK Analysis for Treatment 4: 2.5 mg/Kg of rI2S (5 mL Volume) by SC Injection into Thigh Area Serum concentration-time data from Animal 5324 were excluded from mean calculations and PK analysis, because of insufficient serum concentration data. Anti-I2S antibodies was detected in the serum of this animal with a high-titer (102400) and high concentration (417 ng/mL) prior to Treatment 4.

In the remaining two monkeys, serum concentrations lower than the limit of quantitation (62.5 ng/mL) were observed prior to the start of Treatment 4 (182 and 115 ng/mL in Monkeys 5305 and 5306, respectively). Following SC administration of 2.5 mg/kg of rI2S AF, the absorption phase lasted about 3 hours and which was followed by a terminal elimination phase. Peak concentration (3750±1,527 ng/mL) was observed at approximately 3.5±0.7 hours, followed by an drop in IS2 serum concentration to 1,240±226 ng/mL at approximately 24 hours post dosing. A serum concentrations of 552±126 ng/mL was observed at approximately 48 hours (the last sampling time point in the group), representing 15% of the peak concentration (see Table 12).

Non-compartmental PK parameters were obtained from these two NHPs following Treatment 3, resulting in calculated $AUC_{0-24hour}$ and $AUC_{inf}$ values of approximately 50156±9993 and 87901±208 hr.ng/mL, respectively. The rate of clearance (CL/F) observed was 28±0 mL/hr/kg with a terminal half-life of approximately 20 hours (20.1±2.9, n=2). The calculated distribution volume ($V_z/F$), based on the empirically determined terminal phase, was approximately 823±118 mL/kg (see Table 13).

Compared with those after IV dosing in Treatment 1, SC bioavailability in Treatment 4 was 69.9%, based on the values of $AUC_{inf}$ that had been normalized for dose (see Table 13). The value of $C_{max}$ post SC dosing was 5.9% of that post IV dosing. However, the value of rI2S concentration at 24 hours post SC dosing was about 6.5-fold higher than that post IV dosing (1.3-fold higher when the values of concentrations were normalized for dose). The percentage of AUC extrapolated from last time point to infinity was 18±7% of the $AUC_{inf}$.

TABLE 12

Serum I2S Concentration for Treatment 4: 2.5 mg/kg, 5 mL SC (thigh), n = 3

| Animal ID | 5305 | 5306 | 5324 | Mean | SD | |
|---|---|---|---|---|---|---|
| Time | Concentration | | | ng/mL | ng/mL | N |
| 0 | 182 | 115 | <LLOQ | 99 | 92 | 3 |
| 0.08 | 190 | 168 | <LLO | 179 | 16 | 2 |
| 0.25 | 272 | 1010 | <LLO | 641 | 522 | 2 |
| 0.5 | 545 | 1840 | <LLO | 1193 | 916 | 2 |
| 0.75 | 704 | 1980 | <LLO | 1342 | 902 | 2 |
| 1 | 983 | 2480 | <LLO | 1732 | 1059 | 2 |
| 2 | 1700 | 3920 | <LLO | 2810 | 1570 | 2 |
| 3 | 2580 | 4830 | <LLO | 3705 | 1591 | 2 |
| 4 | 2670 | 4740 | 109 | 2506 | 2320 | 3 |
| 8 | 2400 | 3070 | 104 | 1858 | 1556 | 3 |
| 12 | 1640 | 1890 | 73.8 | 1201 | 984 | 3 |
| 24 | 1400 | 1080 | <LLO | 1240 | 226 | 2 |
| 48 | 641 | 463 | <LLO | 552 | 126 | 2 |

<LLOQ: lower than the limit of quantitation

TABLE 13

PK Analysis for Treatment 4: 2.5 mg/kg, 5 mL/animal, SC dosing into thigh area

| PK | unit | G4- | G4- | | mean | SD | N |
|---|---|---|---|---|---|---|---|
| $t_{1/2}$ | hr | 22.1 | 18.0 | ND | 20.1 | 2.9 | 2 |
| $T_{max}$ | hr | 4.0 | 3.0 | ND | 3.5 | 0.7 | 2 |
| $C_{max}$ | ng/mL | 2670 | 4830 | ND | 3750 | 1527 | 2 |
| $AUC_{0-24\ hr}$ | hr*ng/ | 43090 | 57223 | ND | 50156 | 9993 | 2 |
| $AUC_{inf}$ | hr*ng/ | 88048 | 87755 | ND | 87901 | 208 | 2 |

TABLE 13-continued

PK Analysis for Treatment 4: 2.5 mg/kg,
5 mL/animal, SC dosing into thigh area

| PK | unit | G4- | G4- | | mean | SD | N |
|---|---|---|---|---|---|---|---|
| AUC % $_{extrap}$ | % | 23 | 14 | ND | 18 | 7 | 2 |
| Vz | mL/kg | 907 | 739 | ND | 823 | 118 | 2 |
| CL | mL/hr/k | 28 | 28 | ND | 28 | 0 | 2 |

ND: not determined due to insufficient data

PK Analysis for Treatment 5: 1.0 mg/Kg of rI2S (1 mL Volume) by SC Injection into Thigh Area For experimental Treatment 5, three different NHPs comprising group 2 were used. As in experimental Treatments 1-4, I2S serum concentrations and PK profiles were obtained from each animal. Serum concentrations of I2S greater than the lower limit of quantitation (62.5 ng/mL) were observed in two of the three animals prior to the start of Treatment 4 (94.3 and 77.9 ng/mL in Monkeys 5319 and 5363, respectively). Following SC administration of 1.0 mg/kg of rI2S, the absorption phase of approximately 1 hour was observed. Peak concentration (1770±131 ng/mL) was observed at approximately 1.3±0.6 hours after SC dosing, followed by reduction in I2S serum concentration during elimination phase. I2S concentration of 663±47, 298±53 and 132±33 ng/mL at 24, 48 and 96 hours after dosing were observed, constituting approximately 37%, 17% and 7% of the peak concentration, respectively (see Table 14).

For the three animals of group 2, three animals, $AUC_{0-24\ hour}$ and $AUC_{inf}$ values of approximately 22306±3024 and 50917±4571 hr.ng/mL, respectively; along with a clearance (CL/F) rate of 20±2 mL/hr/kg and terminal half-life of 35.9±14.1 hours. The calculated distribution volume ($V_z/F$), based on the empirically determined terminal phase, was approximately 1000±329 mL/kg (see Table 15).

Compared with those after IV dosing in Treatment 1, SC bioavailability in Treatment 6 was 101.3%, based on the values of $AUC_{inf}$ that had been normalized for dose (see Table 15). These observations strongly suggest that rI2S was absorbed from the injection site effectively and almost completely. The value of $C_{max}$ was 6.9% of that post IV dosing. However, the value of rI2S concentration at 24 hours post SC dosing was about 3.5-fold higher than that post IV dosing (about 1.7-fold when the values of concentrations were normalized for dose). The percentage of AUC extrapolated from last time point to infinity was 14±8% of the $AUC_{inf}$. The extrapolation of AUC from last time point to infinity was based on the concentration data from 0 to 48 hours in Groups 2, 3 and 4, while from 0 to 96 hours in Group 5. The percentages of the extrapolations were 31±24%, 30±19% and 18±7% in Groups 2, 3 and 4, respectively, while 14±8% in Group 5.

These data suggest that SC injection at both the 1.0 mg/kg (Treatment 4) and 2.5 mg/kg (Treatment 5) doses into the thigh region, resulted in a considerable bioavailability and serum concentration as compared to IV administration. Similar to the data generated for SC injection into the scapula, these surprising findings strongly suggest that SC injection into the thigh results in a rapid uptake and distribution of I2S into the serum. Even more surprising, are the findings that SC injection, independent of its site of injection (scaplula or thigh), demonstrated a bioavailability almost as large as the expected theoretical maximum bioavailability of IV administration. Contrary to conventional pharmacological paradigms, these finding suggest that SC administration may represent an effective way to distribute I2S throughout the body. In addition, such approach could be even more promising when used in conjunction with other therapeutic approaches that separately target the CNS.

TABLE 14

Serum I2S Concentration for Treatment 5: 1.0 mg/kg, 1 mL SC (thigh), n = 3

| Time (hour) | 5319 | 5265 | 5363 | Mean | SD | N |
| | Concentration (ng/mL) | | | ng/mL | ng/mL | |
|---|---|---|---|---|---|---|
| 0 | 94.3 | 0 | 77.9 | 57.4 | 50.4 | 3 |
| 0.08 | 239 | 121 | 142 | 167.3 | 62.9 | 3 |
| 0.25 | 878 | 786 | 469 | 711.0 | 214.6 | 3 |
| 0.5 | 1380 | 1240 | 977 | 1199.0 | 204.6 | 3 |
| 1 | 1920 | 1670 | 1710 | 1766.7 | 134.3 | 3 |
| 2 | 1370 | 1680 | 1580 | 1543.3 | 158.2 | 3 |
| 4 | 1220 | 1190 | 1520 | 1310.0 | 182.5 | 3 |
| 8 | 976 | 752 | 1220 | 982.7 | 234.1 | 3 |
| 12 | 819 | 529 | 979 | 775.7 | 228.1 | 3 |
| 24 | 716 | 647 | 626 | 663.0 | 47.1 | 3 |
| 48 | 340 | 316 | 238 | 298.0 | 53.3 | 3 |
| 72 | 219 | 236 | 129 | 194.7 | 57.5 | 3 |
| 96 | 136 | 162 | 96.4 | 131.5 | 33.0 | 3 |

<LLOQ: lower than the limit of quantitation

TABLE 15

PK Analysis for Treatment 5: 1.0 mg/kg, 1.0 mL/animal, SC dosing into thigh area

| PK Parameter | unit | G6-5265 | G6-5319 | G6-5363 | mean | SD | N |
|---|---|---|---|---|---|---|---|
| $t_{1/2}$ | hr | 49.8 | 36.3 | 21.6 | 35.9 | 14.1 | 3 |
| $T_{max}$ | hr | 2.0 | 1.0 | 1.0 | 1.3 | 0.6 | 3 |
| $C_{max}$ | ng/mL | 1680 | 1920 | 1710 | 1770 | 131 | 3 |
| $AUC_{0-24\ hr}$ | hr*ng/mL | 19110 | 22643 | 25166 | 22306 | 3042 | 3 |
| $AUC_{inf}$ | hr*ng/mL | 53704 | 53407 | 45642 | 50917 | 4571 | 3 |

TABLE 15-continued

PK Analysis for Treatment 5: 1.0 mg/kg, 1.0 mL/animal, SC dosing into thigh area

| PK Parameter | unit | G6-5265 | G6-5319 | G6-5363 | mean | SD | N |
|---|---|---|---|---|---|---|---|
| AUC % $_{extrap}$ | % | 22 | 13 | 7 | 14 | 8 | 3 |
| Vz | mL/kg | 1338 | 981 | 682 | 1000 | 329 | 3 |
| CL | mL/hr/kg | 19 | 19 | 22 | 20 | 2 | 3 |

ND: not determined due to insufficient data

Comparison of Bioavailability Between Different Experimental Treatments

The individual PK parameters ($C_{max}$, $AUC_{inf}$ and $AUC_{0-24\ hr}$) for each of experimental Treatments 1-5 were normalized based on concentration. Normalized values for experimental Treatments 2-5 were then compared to IV administration (Treatment 1), which was designed to represent the maximum theoretical bioavailability (Table 16). Consistent with the findings above, the data suggests that rI2S was absorbed into the serum effectively and almost completely after subcutaneously administration, as indicated by SC bioavailability of approximately 100%. The data also suggests that recombinant I2S SC administration resulted in higher serum levels than that observed after IV dosing at some late time points. This is indicated by the data of experimental Treatment 5, in which about 7% of peak concentration was detected beyond 96 hours post SC dosing of 1 mg/kg rI2S (immeasurable at 48 hours after IV dosing) and that serum concentration after SC injection was about 1.2- to 1.7-fold higher than that post IV dosing at 24 hours at the same dose level. Furthermore, the rate of clearance was 20 mL/hr/kg with a half-life about 1.5 days (35.9±14.1 hours) after SC dosing 1 mg/kg. This suggests a longer exposure time within the body after SC dosing.

TABLE 16

Comparison of bioavailability between different treatments

| Exposure | Group | PK | Dose | Value/Dose$^{(a)}$ | Comparison | Ratio |
|---|---|---|---|---|---|---|
| $C_{max\ (ng/mL)}$ | 1 | 12760 | 0.5 | 25520 | ND | ND |
| | 2 | 2457 | 2.5 | 983 | Group 2: 1 | 3.9 |
| | 3 | 8927 | 10 | 893 | Group 3: 1 | 3.5 |
| | 4$^{(b)}$ | 3750 | 2.5 | 1500 | Group 4: 1 | 5.9 |
| | 6 | 1770 | 1 | 1770 | Group 5: 1 | 6.9 |
| $AUC_{inf}$ (hr · ng/mL) | 1 | 25140 | 0.5 | 50280 | ND | ND |
| | 2 | 82770 | 2.5 | 33108 | Group 2: 1 | 65.8 |
| | 3 | 316435 | 10 | 31644 | Group 3: 1 | 62.9 |
| | 4$^{(b)}$ | 87901 | 2.5 | 35160 | Group 4: 1 | 69.9 |
| | 5 | 50917 | 1 | 50917 | Group 5: 1 | 101.3 |
| $AUC_{0-24\ hr}$ (hr · ng/mL) | 1 | 22267 | 0.5 | 44534 | ND | ND |
| | 2 | 31062 | 2.5 | 12425 | Group 2: 1 | 27.9 |
| | 3 | 143291 | 10 | 14329 | Group 3: 1 | 32.2 |
| | 4$^{(b)}$ | 50156 | 2.5 | 20062 | Group 4: 1 | 45 |
| | 5 | 22306 | 1 | 22306 | Group 5: 1 | 50.1 |

$^{(a)}$PK values are normalized for dose.
$^{(b)}$Data from Monkey 5324 were excluded from mean calculation.
ND: not done Example 2

IV and Subcutaneous (SC) Administration of Recombinant Iduronate 2-Sulfatase in Mice The purpose of the present example, was to perform a study to evaluate subcutaneous (SC) administration of a recombinant form of iduronate-2-sulfatase (rI2S). As part of the evaluation, pharmacokinetic and pharmacodynamic parameters were empirically determined following SC administration, using a mouse experimental model system. Such data may be used to help extrapolate and predict conditions for SC administration in humans in order to design an effective therapeutic regimen, while taking into consideration the drug's safety profile.

Experimental Parameters for Pharmacokinetic Evaluation

For the pharmacokinetic studies, three groups of three male mice were selected for evaluating the effectiveness of subcutaneous treatment of recombinant iduronate-2-sulfatase (rI2S) as compared to IV administration. Groups 1 through 3, consisted of three naïve male C57bl/6 I2S knock-out (IKO) mice treated with a single IV or subcutaneous dose of rI2S, at varying concentrations (Table 17).

Replacement Enzyme

For the study, a single lot of an enzymatically active recombinant humanized version of Iduronate-2-sulfatase was used. Recombinant I2S was stably formulated in a 0.9% saline solution at a working concentration of 2.5 mg/ml. Concentration of rI2S in each dose formulation was analyzed using a qualified spectrophotometric method involving absorbance at a wavelength of 280 nm.

TABLE 17

Experimental Groups, Dosing routes, doses and collection time points

| Experimental Group | N | Route | Dose mg/kg | Serum Collection Time points |
|---|---|---|---|---|
| 1 | 3 | IV | 0.5 | 5, 15, 30 min; 1, 2, 4, 6, 8, 10, 24 and 36 hours post dose |
| 2 | 3 | SC | 1.0 | 5, 15, 30, 45 min; 1, 2, 4, 6, 8, 12, 24, 48, 72 and 96 hours post dose |
| 3 | 3 | SC | 2.5 | |

Serum was processed and collected from the blood samples obtained at each time point within experimental treatment groups 1-3, and stored frozen at −65 to −85° C. until analysis. Serum concentration of I2S was analysed using an I2S-specific ELISA and expressed in ng/mL of serum.

Individual serum concentration-time data were analysed using well established non-compartmental models to determine pharmacokinetic (PK) parameters for I2S administration. The use of standard PK equations and formula rearrangement (See Example 1), were used to calculate AUC (Area under the Concentration Time Curve) values, and to extrapolate subsequent pharmacokinetic parameters such as: Maximum observed serum concentration ($C_{max}$, ng/mL); Time of $C_{max}$ appearance in the serum ($T_{1/2}$, hours); area under the serum concentration-time curve from time zero to the last sampling time at which serum concentrations were measurable ($AUC_{last}$, hr.ng/mL); Area under the serum concentration-time curve extrapolated to infinity ($AUC_{inf}$, hr.ng/mL); Terminal half-life ($t_{1/2}$, hours); Total clearance (CL, mL/hr/kg) calculated as dose/$AUC_{inf}$; and Bioavailability (F) calculated as $AUC_{inf(SC)}/AUC_{inf(IV)}*100\%$, based on $AUC_{inf}$ values that was normalized for dose (Table 18).

TABLE 18

Comparison of PK parameters and bioavailability between different treatments

| PK Parameter | units | Experimental Groups | | |
|---|---|---|---|---|
| | | IV (0.5 mg/kg) | SC (1.0 mg/kg) | SC (2.5 mg/kg) |
| $t_{1/2}$ | hr | 2.8 | 7.8 | 8.2 |
| $T_{max}$ | hr | 0.08 | 4 | 0.25 |
| $C_{max}$ | ng/mL | 8494 | 322 | 852 |
| $AUC_{last}$ | hr*ng/mL | 6659 | 2727 | 6273 |
| $AUC_{inf}$ | hr*ng/mL | 6664 | 2749 | 6379 |
| CL | mL/hr/kg | 75 | 364 | 392 |
| F(%) | N/A | — | 20.6 | 19.1 |

Comparison of Bioavailability Between Different Experimental Treatments

Figure 8:
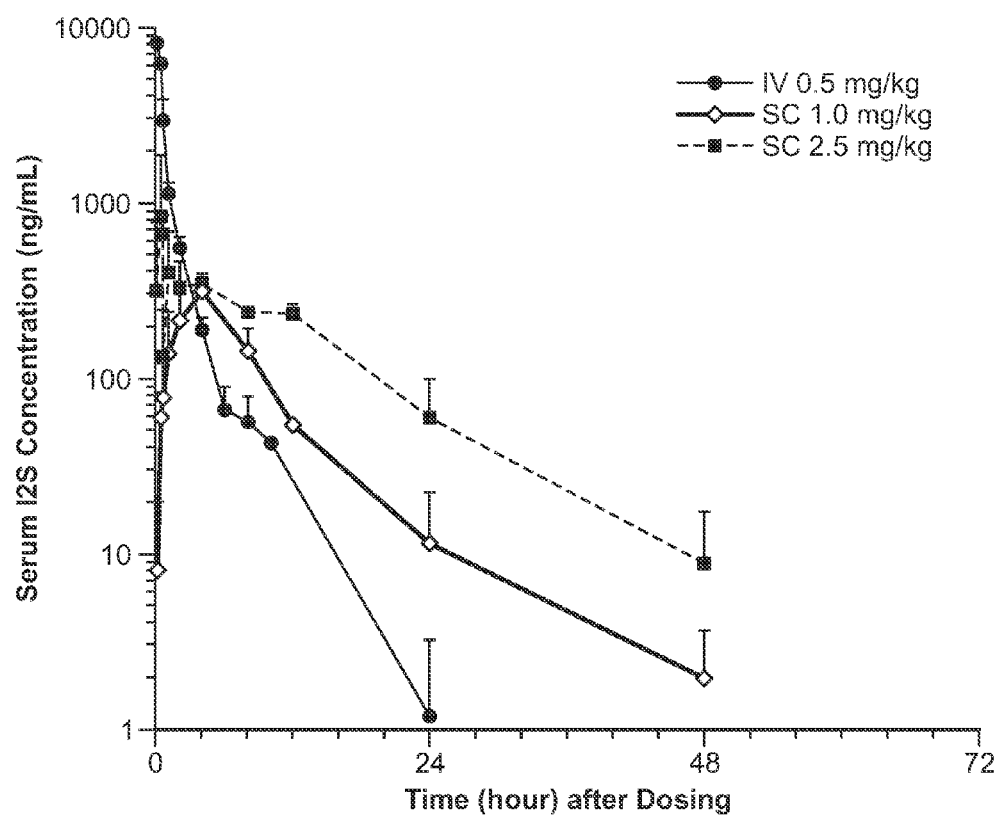
FIG. 8 illustrates exemplary data comparing serum concentration as a function of time in C57bl/6 I2S knockout (IKO) or WT mice, for three different experimental treatment groups (G1-G3).
Figure 9:
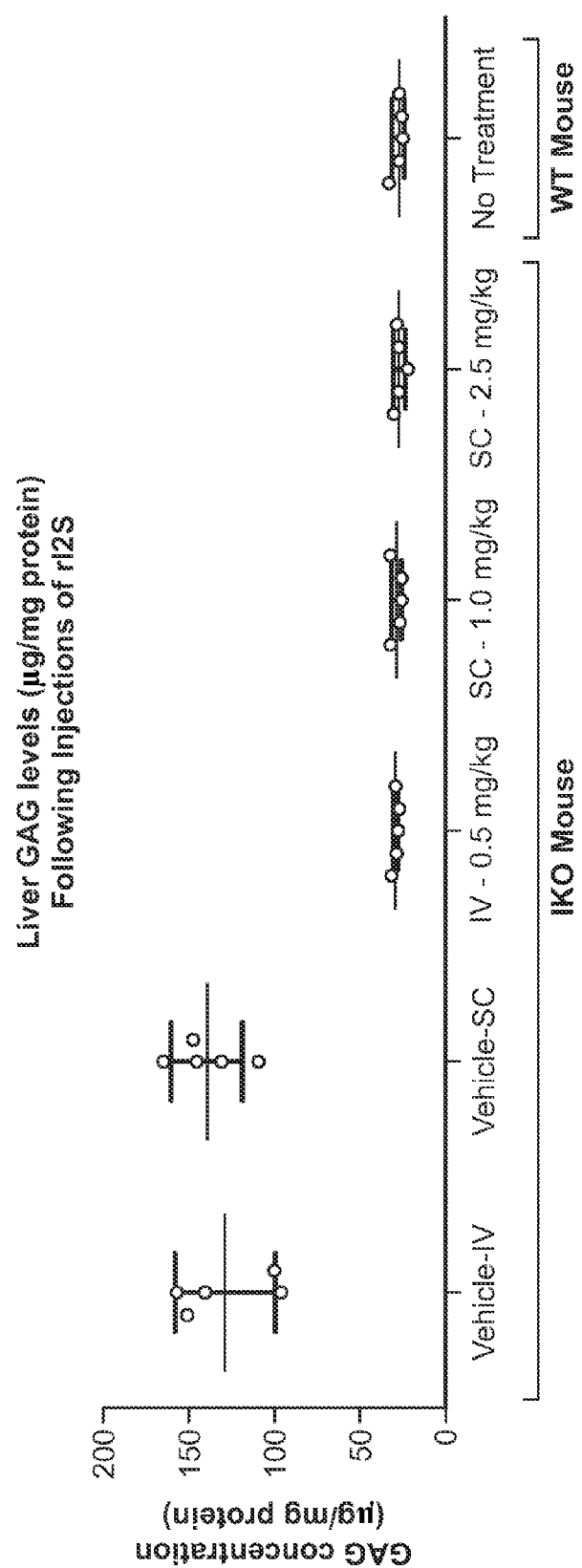
FIG. 9 illustrates exemplary data comparing glycosaminoglycan (GAG) levels within the liver of C57bl/6 I2S knockout (IKO) or WT mice, following intravenous (IV) or subcutaneous (SC) treatment at various concentrations.
Figure 10:
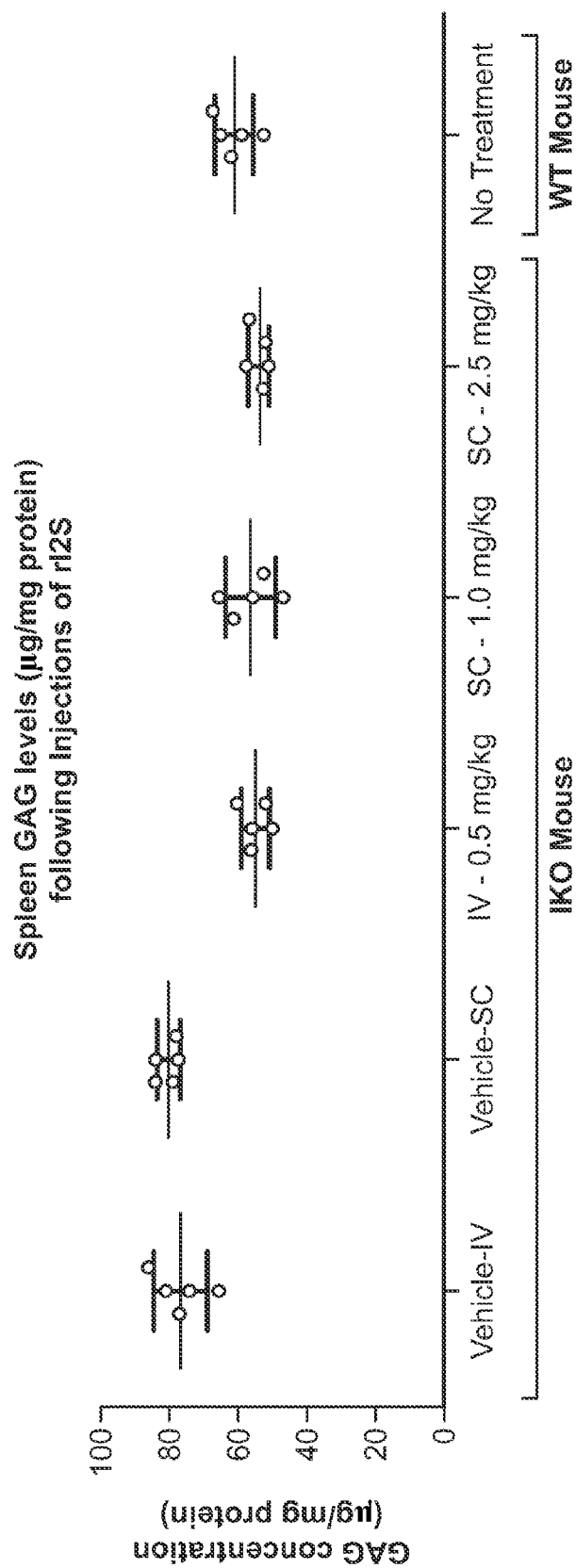
FIG. 10 illustrates exemplary data comparing glycosaminoglycan (GAG) levels within the Spleen of C57bl/6 I2S knockout (IKO) or WT mice, following intravenous (IV) or subcutaneous (SC) treatment at various concentrations.
Figure 11:
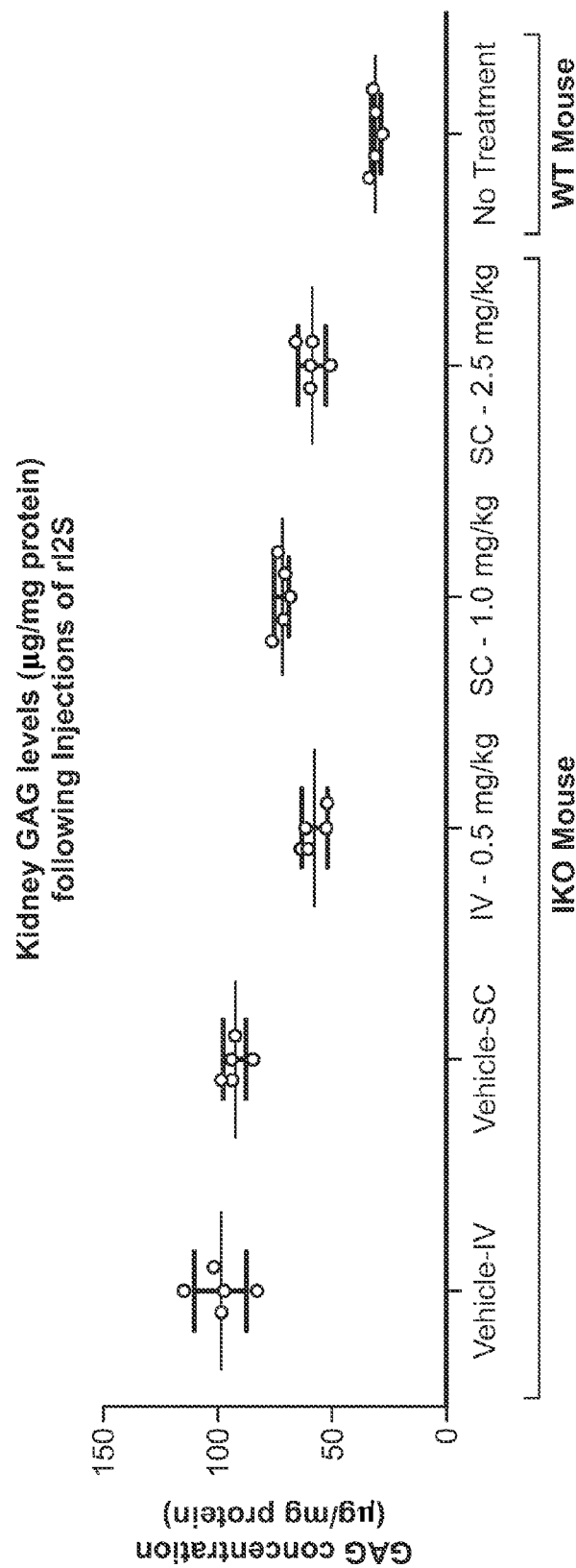
FIG. 11 illustrates exemplary data comparing glycosaminoglycan (GAG) levels within the kidney of C57bl/6 I2S knockout (IKO) or WT mice, following intravenous (IV) or subcutaneous (SC) treatment at various concentrations.
Figure 12:
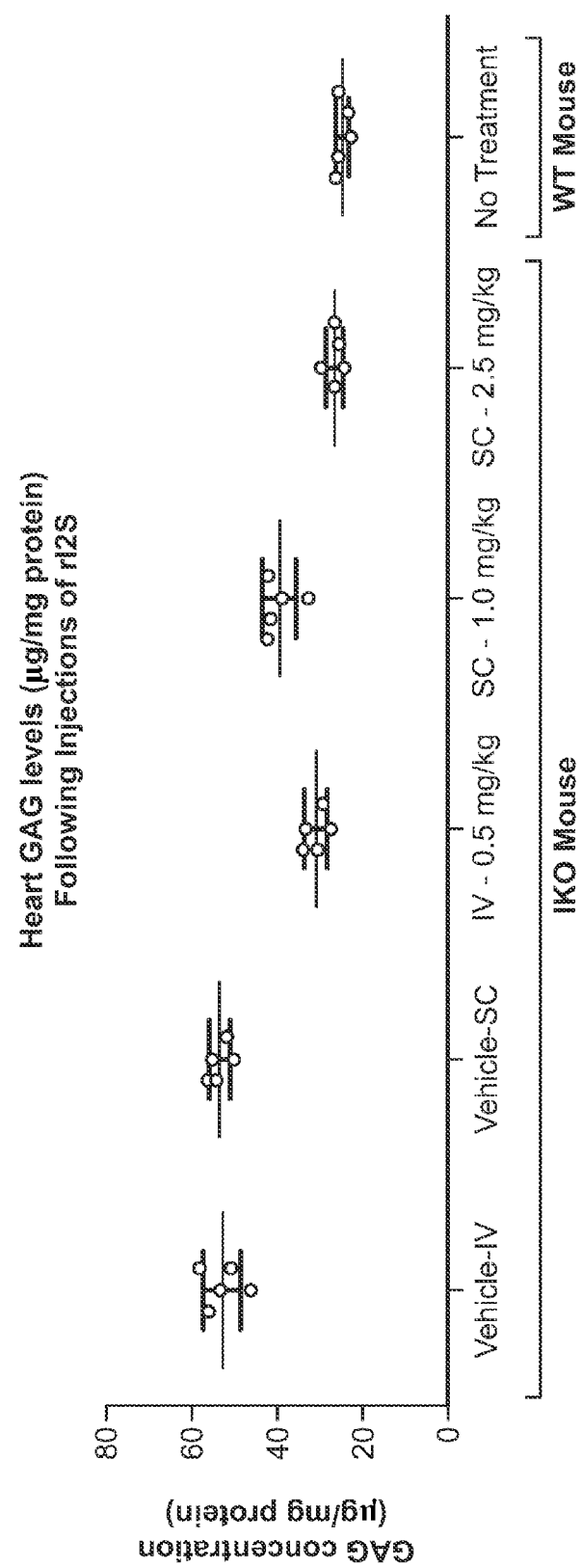
FIG. 12 illustrates exemplary data comparing glycosaminoglycan (GAG) levels within the heart of C57bl/6 I2S knockout (IKO) or WT mice, following intravenous (IV) or subcutaneous (SC) treatment at various concentrations.

These data demonstrate that SC injection at both the 1.0 mg/kg and 2.5 mg/kg doses, were taken up directly into the circulating blood supply; reaching a peak concentration approximately 4 hours after administration. Contrary to IV injection, rI2S administered by subcutaneous injection remained in the blood supply for a longer duration of time, with serum rI2S levels detected as far out as 48 hours post injection (FIG. 8). During clinical treatment prolonged, slow release of rI2S into the blood supply may be advantageous in allowing additional time for cellular uptake and endocytosis by the surrounding cells, prior to renal clearance and removal from the body.

Experimental Parameters for Pharmacodynamic Evaluation

Iduronate-2-sulfatase is one of several lysosomal enzymes responsible for mediating the systematic degradation and turnover of glycosaminoglycans (GAGs) within the body. Therefore, changes in glycosaminoglycan concentration within the tissues and fluids of the body, can be used to compare the pharmacodynamics properties of subcutaneous and IV delivery of recombinant iduronate-2-sulfatase (rI2S) and its therapeutic potential. For the study, six groups of five male mice were selected. Experimental groups 1 through 5 consisted of five naïve male C57bl/6 I2S knockout (IKO) mice treated with a single IV or subcutaneous dose of saline control or rI2S at varying concentrations (Table 19). Injections were administered once a week over a four week period on days 1, 8, 15, 22 and 29. Experimental group 6 represented the experimental control, which consisted of five naïve male C57bl/6 wild-type mice that did not receive any injection, but were maintained under the same living conditions. Total urine output was collected 24 hours prior to the start of the experiment and then again in the 24 hour period prior to each weekly injection. Approximately 24 hours after administering the final injection on day 29, all five mice within each experimental group were sacrificed, perfused with sterile saline and the liver, spleen, kidney and heart removed. All tissue and urine samples collected were snap frozen and stored at −65 to −85° C. until analysis.

TABLE 19

Dosing routes, doses, collection time points

| Group | (N) | Genotype | Dose (mg/kg) | Route | Dosing Schedule |
|---|---|---|---|---|---|
| 1 | 5 | IKO | 0.0 | IV | Days 1, 8, 15, 22 and 29 |
| 2 | 5 | | 0.0 | SC | |
| 3 | 5 | | 0.5 | IV | |
| 4 | 5 | | 1.0 | SC | |
| 5 | 5 | | 2.5 | SC | |
| 6 | 5 | WT | NA | NA | NA |

Replacement Enzyme

For the study, a single lot of an enzymatically active recombinant humanized version of Iduronate-2-sulfatase was used. Recombinant I2S was stably formulated in a 0.9% saline solution at a working concentration of 2.5 mg/ml. Concentration of rI2S in each dose formulation was analyzed using a qualified spectrophotometric method involving absorbance at a wavelength of 280 nm.

Collected tissue samples were thawed and analysed for glycosaminoglycan levels by Dimethyl Methylene Blue (DMB) Assay. Briefly, tissue samples were stained for heparan sulfate by treating the sample with 1,9-dimethylmethylene blue dye resuspended in formic acid at a pH of 3.3, and measured for absorbance at wave length of 520 nm. Total protein concentration within each tissue sample was determined using a BCA assay and used to normalize for the concentration of heparan sulfate calculated within each tissue sample. The raw data for each tissue type is presented in tables 20-23 and visually represented in FIGS. 9-12. These findings demonstrate that SC administration of 1.0 mg/kg or 2.5 mg/kg of rI2S significantly reduced tissue GAG levels compared to vehicle control. In addition, the data suggests that SC administration at 2.5 mg/kg resulted in a similar reduction in tissue GAG levels compared to 0.5 mg/kg IV for all four tissues tested. Furthermore, these findings suggest that SC injection of rI2S is able to effectively enter the blood stream and is taken up by the peripheral tissues of the body to degrade herparan sulfate within the lysosome of the cell.

TABLE 20

Comparison of Liver GAG levels for IV versus SC delivery of rI2S
Liver GAG (µg/mg protein)

| Group | Dose (mg/kg) | Route | Genotype | Mean ± SD (Median) |
|---|---|---|---|---|
| 1 | 0.0 | IV | IKO | 129.2 ± 29.0 (141.0) |
| 2 | 0.0 | SC | | 139.8 ± 20.7 (145.3) |
| 3 | 0.5 | IV | | 29.2 ± 1.4 (28.7) |
| 4 | 1.0 | SC | | 28.5 ± 2.8 (26.9) |
| 5 | 2.5 | SC | | 27.0 ± 3.1 (27.5) |
| 6 | Untreated | NA | WT | 27.8 ± 3.1 (27.2) |

TABLE 21

Comparison of Spleen GAG levels for IV versus SC delivery of rI2S
Spleen GAG (µg/mg protein)

| Group | Dose (mg/kg) | Route | Genotype | Mean ± SD (Median) |
|---|---|---|---|---|
| 1 | 0.0 | IV | IKO | 77.3 ± 7.7 (77.6) |
| 2 | 0.0 | SC | | 81.0 ± 3.2 (79.5) |
| 3 | 0.5 | IV | | 55.2 ± 4.1 (56.4) |
| 4 | 1.0 | SC | | 56.7 ± 7.3 (55.8) |
| 5 | 2.5 | SC | | 54.3 ± 2.9 (52.9) |
| 6 | Untreated | NA | WT | 61.6 ± 5.7 (62.4) |

TABLE 22

Comparison of Kidney GAG levels for IV versus SC delivery of rI2S
Kidney GAG (µg/mg protein)

| Group | Dose (mg/kg) | Route | Genotype | Mean ± SD (Median) |
|---|---|---|---|---|
| 1 | 0.0 | IV | IKO | 98.8 ± 11.5 (98.2) |
| 2 | 0.0 | SC | | 92.3 ± 4.9 (93.4) |
| 3 | 0.5 | IV | | 57.4 ± 5.2 (59.7) |
| 4 | 1.0 | SC | | 71.8 ± 2.8 (70.9) |
| 5 | 2.5 | SC | | 58.6 ± 5.6 (59.2) |
| 6 | Untreated | NA | WT | 30.4 ± 2.1 (30.1) |

TABLE 23

Comparison of Heart GAG levels for IV versus SC delivery of rI2S
Heart GAG (µg/mg protein)

| Group | Dose (mg/kg) | Route | Genotype | Mean ± SD (Median) |
|---|---|---|---|---|
| 1 | 0.0 | IV | IKO | 53.1 ± 4.5 (53.5) |
| 2 | 0.0 | SC | | 53.6 ± 2.4 (54.3) |
| 3 | 0.5 | IV | | 31.0 ± 2.6 (30.6) |
| 4 | 1.0 | SC | | 39.6 ± 4.0 (41.6) |
| 5 | 2.5 | SC | | 26.6 ± 2.0 (26.2) |
| 6 | Untreated | NA | WT | 24.7 ± 1.4 (25.5) |

Figure 13:
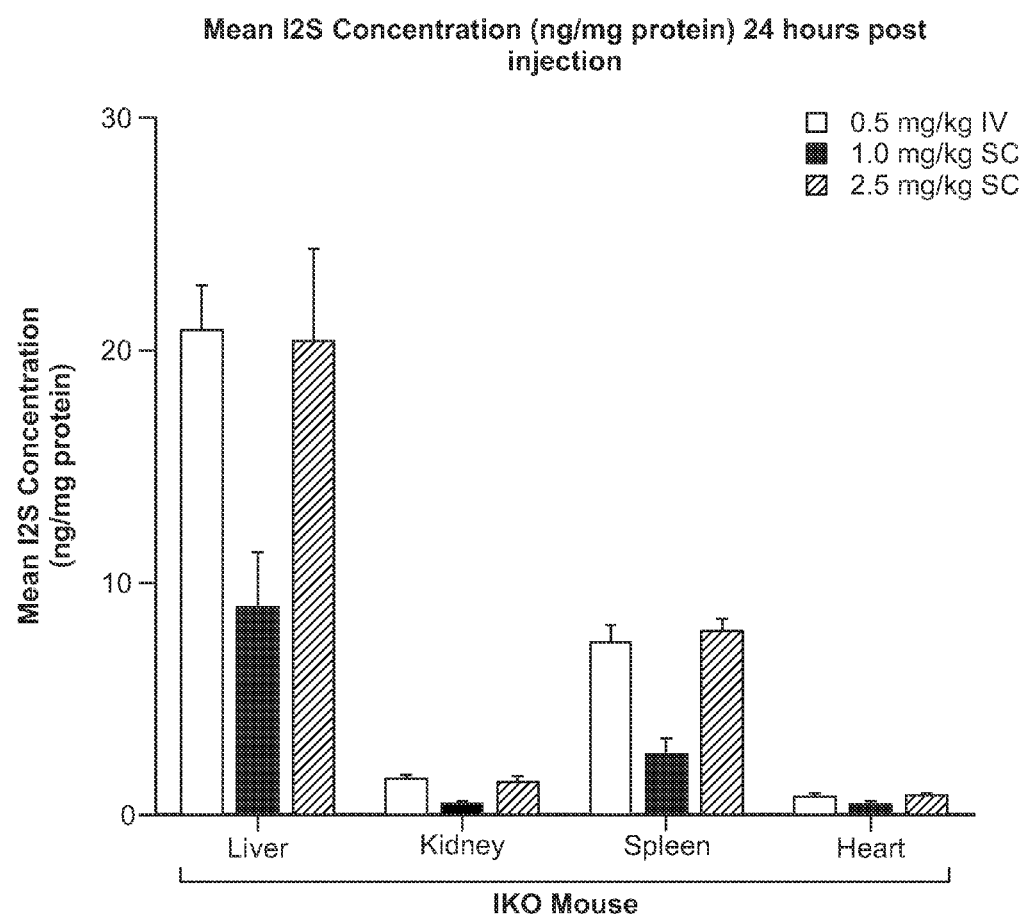
FIG. 13 illustrates exemplary data comparing I2S concentration (ng/mg protein) 24 hours post intravenous (IV) or subcutaneous (SC) injection at various concentrations.

In addition to identifying heparan sulfate as a measure of I2S activity, analysis was performed to determine the tissue concentration levels of I2S in each IKO and WT experimental group. Briefly, tissue collected during the experiment was digested, processed for protein removal and subjected to an I2S-specific ELISA. The concentration of I2S was calculated by normalizing against total protein concentration and expressed in ng/mL of total cellular protein. The raw data for each experimental group is presented in Table 24 and visually represented in FIG. 13. As demonstrated in FIG. 13, the data demonstrates that both the 1.0 mg/kg and 2.5 mg/kg SC injection resulted in the accumulation and cellular uptake of I2S within the peripheral tissues of the body. In addition, SC injection of 2.5 mg/kg of rI2S resulted in a cellular concentration of I2S similar to that of 0.5 mg/kg IV injection, when examined 24 hours post injection (FIG. 13).

TABLE 24

I2S protein levels in various tissues from IKO mice following SC and IV injection

| | Dose | | | Tissue I2S Concentration (ng/mg protein) ± SD (median) | | | |
|---|---|---|---|---|---|---|---|
| Group | (mg/kg) | Route | Mouse | Liver | Kidney | Spleen | Heart |
| 1 | 0.0 | IV | IKO | 0.0 ± 0.0 (0.0) | 0.0 ± 0.0 (0.0) | 0.0 ± 0.0 (0.0) | 0.0 ± 0.0 (0.0) |
| 2 | 0.0 | SC | | 0.0 ± 0.0 (0.0) | 0.0 ± 0.0 (0.0) | 0.0 ± 0.0 (0.0) | 0.0 ± 0.0 (0.0) |
| 3 | 0.5 | IV | | 20.6 ± 2.3 (20.41) | 1.3 ± 0.1 (1.3) | 7.2 ± 0.9 (6.6) | 0.5 ± 0.1 (0.5) |
| 4 | 1.0 | SC | | 8.7 ± 2.6 (7.7) | 0.2 ± 0.1 (0.2) | 2.3 ± 1.0 (1.8) | 0.2 ± 0.1 (0.2) |
| 5 | 2.5 | SC | | 20.2 ± 4.1 (20.3) | 1.2 ± 0.3 (1.0) | 7.6 ± 0.7 (8.0) | 0.6 ± 0.2 (0.5) |
| 6 | NA | NA | WT | 0.0 ± 0.0 (0.0) | 0.0 ± 0.0 (0.0) | 0.0 ± 0.0 (0.0) | 0.0 ± 0.0 (0.0) |

Figure 14:
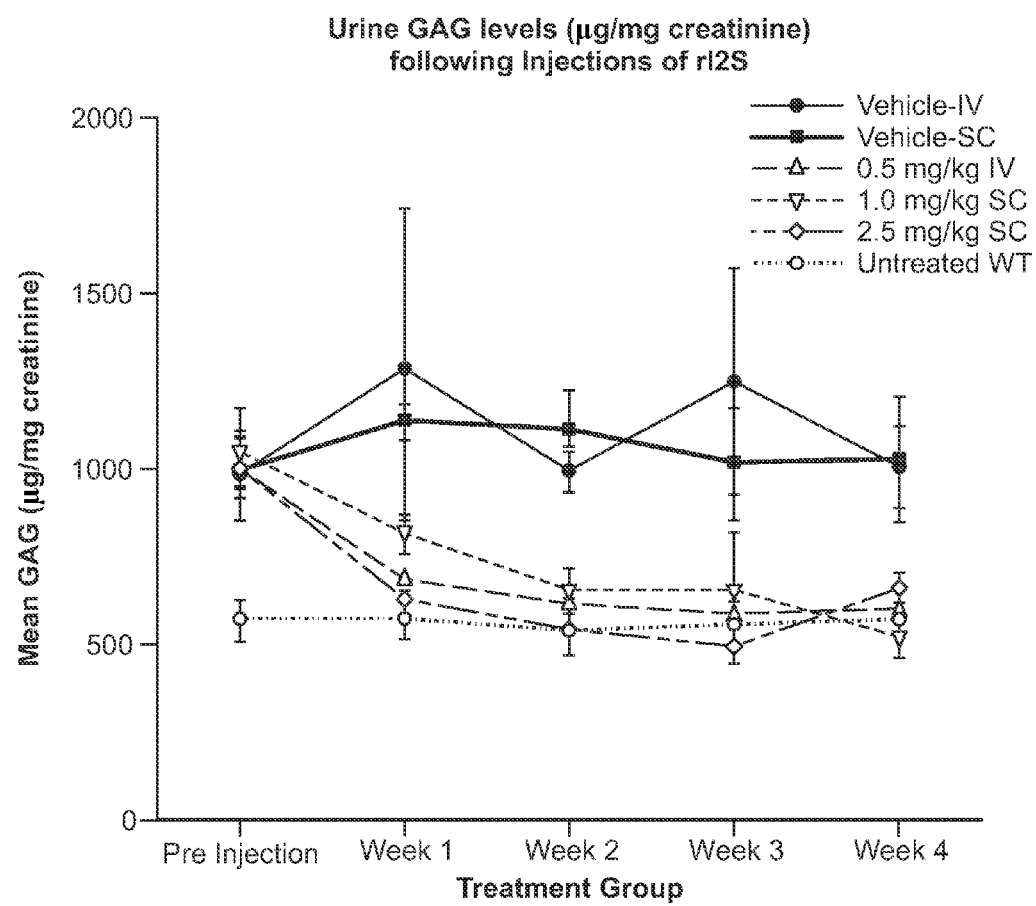
FIG. 14 illustrates exemplary data comparing urine glycosaminoglycan (GAG) levels over a four week period, following intravenous (IV) or subcutaneous (SC) treatment at various concentrations.

Urine samples collected during the study were also analysed for glycosaminoglycan levels using a Dimethyl Methylene Blue (DMB) Assay. Briefly, urine samples were stained for heparan sulfate by treating the sample with 1,9-dimethylmethylene blue dye resuspended in formic acid at a pH of 3.3, and measured for absorbance at a wave length of 520 nm. The concentration of heparan sulfate was normalized normalized using the total concentration of creatinine protein identified in the urine sample. The raw data for each experimental group over the four week period is presented in Table 25 and is visually represented in FIG. 14. The findings demonstrate that SC administration of 1.0 mg/kg or 2.5 mg/kg of rI2S significantly reduced urine GAG levels in IKO mice compared to vehicle control. In addition, the data suggests that SC administration at 2.5 mg/kg resulted in a similar reduction in tissue GAG levels compared to 0.5 mg/kg IV. Taken together, these findings further support the tissue studies and suggest that SC injection of rI2S is able to effectively enter the blood stream. More importantly, the rI2S is taken up by the peripheral tissue and is biologically active; as indicated by a dramatic reduction in urine secretion of heparan sulfate. Thus, strongly suggesting that SC delivery of rI2S in not only an effective form of delivery, comparable to that of IV, but it represents a potentially efficacious treatment for a lysosomal storage disease.

TABLE 25

Comparison of Urine GAG levels for IV versus SC delivery of rI2S
Urine GAG (μg/mg protein) ± SD

| Group | Dose (mg/kg) | Route | Mouse | Pre | Week 1 | Week 2 | Week 3 | Week 4 |
|---|---|---|---|---|---|---|---|---|
| 1 | 0.0 | IV | IKO | 977.2 ± 126.2 | 1281.7 ± 456.9 | 993.3 ± 62.1 | 1247.6 ± 320.6 | 1001.8 ± 117.8 |
| 2 | 0.0 | SC | | 988.1 ± 40.0 | 1131.8 ± 50.9 | 1104.9 ± 113.8 | 1013.2 ± 157.5 | 1025.3 ± 180.9 |
| 3 | 0.5 | IV | | 989 ± 57.7 | 684.2 ± 30.2 | 618.7 ± 49.4 | 583.9 ± 42.6 | 607.4 ± 53.8 |
| 4 | 1.0 | SC | | 1040.3 ± 126 | 807.1 ± 55.1 | 656.2 ± 59.1 | 653.1 ± 159.5 | 527.9 ± 63.5 |
| 5 | 2.5 | SC | | 998.1 ± 88.2 | 627.7 ± 52.8 | 541.7 ± 84.7 | 496.6 ± 52.4 | 655.2 ± 48.5 |
| 6 | NA | NA | WT | 566.1 ± 57.5 | 573.1 ± 57.5 | 537.4 ± 63.0 | 553.5 ± 23.5 | 568.4 ± 43.6 |

Example 3

IV and Subcutaneous (SC) Administration of Recombinant Iduronate 2-Sulfatase in Pig The purpose of the present example, was to perform a study to evaluate subcutaneous (SC) administration of a recombinant form of iduronate-2-sulfatase (rI2S). As part of the evaluation, pharmacokinetic parameters were empirically determined following SC administration, using a Gottingen minipig experimental model system. Such data may be used to help extrapolate and predict conditions for SC administration in humans in order to design an effective therapeutic regimen, while taking into consideration the drug's safety profile.

Experimental Parameters for Pharmacokinetic Evaluation

For the pharmacokinetic study, four groups of three male pigs were selected for evaluating the effectiveness of subcutaneous delivery of recombinant iduronate-2-sulfatase (rI2S) as compared to IV administration. Groups 1 through 3 consisted of three naïve male Gottingen minipigs treated with a single IV or subcutaneous dose of rI2S (Lot 11-137), at varying concentrations (Table 26). Group 4 consisted of three non-naïve male Gottingen minipigs treated with a single subcutaneous dose of rI2S (Lot 11-92) at a concentration of 1.0 mg/kg.

TABLE 26

Experimental groups, Dosing routes, lots and doses

| Experimental Group | N | Lot # | Route | Dose mg/kg | Dose Volume (ml/kg) | Serum Collection Time Points |
|---|---|---|---|---|---|---|
| 1 | 3 | 11-137 | IV | 0.5 | 0.1 | 5, 15, 30, 45 min; |
| 2 | 3 | | SC | 1.0 | | 1, 2, 4, 6, 8, 12, |
| 3 | 3 | | SC | 2.5 | | 24, 48 and 72 |
| 4[a] | 3 | 11-92 | SC | 1.0 | | hours post dose |

[a] Animals used for Group 4 were reused from group 1, following an ~7-day washout Replacement Enzyme For the study, two lots of an enzymatically active recombinant humanized version of Iduronate-2-sulfatase were used. Lot 11-137 was stably formulated in a 0.9% saline solution at a working concentration of 2.5 mg/ml. Lot 11-137 was stably formulated in a solution of 20 mM sodium phosphate, 137 mM sodium chloride at pH 6.0 at a working concentration of 2.5 mg/ml. Concentration of rI2S in each dose formulation was analyzed using a qualified spectrophotometric method involving absorbance at a wavelength of 280 nm.

Serum was processed and collected from the blood samples obtained at each time point within experimental treatment groups 1-4, and stored frozen at −65 to −85° C. until analysis. Serum concentration of I2S was analysed using an I2S-specific ELISA and expressed in ng/mL of serum.

Individual serum concentration-time data were analysed using well established non-compartmental models to determine pharmacokinetic (PK) parameters for I2S administration. The use of standard PK equations and formula rearrangement (See Example 1), were used to calculate AUC (Area under the Concentration Time Curve) values, and to extrapolate subsequent pharmacokinetic parameters such as: Maximum observed serum concentration ($C_{max}$, ng/mL); Time of $C_{max}$ appearance in the serum ($T_{max}$, hours); area under the serum concentration-time curve from time zero to the last sampling time at which serum concentrations were measurable ($AUC_{last}$, hr.ng/mL); Area under the serum concentration-time curve extrapolated to infinity ($AUC_{inf}$, hr.ng/mL); Terminal half-life ($t_{1/2}$, hours); Total clearance (CL, mL/hr/kg) calculated as dose/$AUC_{inf}$, and Bioavailability (F) calculated as $AUC_{inf(SC)}/AUC_{inf(IV)}*100\%$, based on $AUC_{inf}$ values that was normalized for dose (Table 27). For the experiment, a cut off of 62.5 ng/ml was established representing the lowest limit of quantitation using the I2S-specific Elisa assay.

TABLE 27

Comparison of PK parameters and bioavailability between different treatments

| PK Parameter | Units | Group 1 IV (0.5 mg/kg) | Group 2 SC (1.0 mg/kg) | Group 3 SC (2.5 mg/kg) | Group 4 SC (1.0 mg/kg) |
|---|---|---|---|---|---|
| $t_{1/2}$ | hr | 7.8 | 13.9 | 15 | 19.4 |
| $T_{max}$ | hr | 0.08 | 3 | 4.7 | 1.5 |
| $C_{max}$ | ng/mL | 11333 | 1028 | 2460 | 933 |
| $AUC_{last}$ | hr*ng/mL | 14621 | 12226 | 42323 | 23344 |
| $AUC_{inf}$ | hr*ng/mL | 15781 | 17219 | 44418 | 25895 |
| CL | mL/hr/kg | 32 | 59 | 57 | 40 |
| F(%) | N/A | — | 54.6 | 56.3 | 82.0 |

Comparison of Bioavailability Between Different Experimental Treatments

Figure 15:
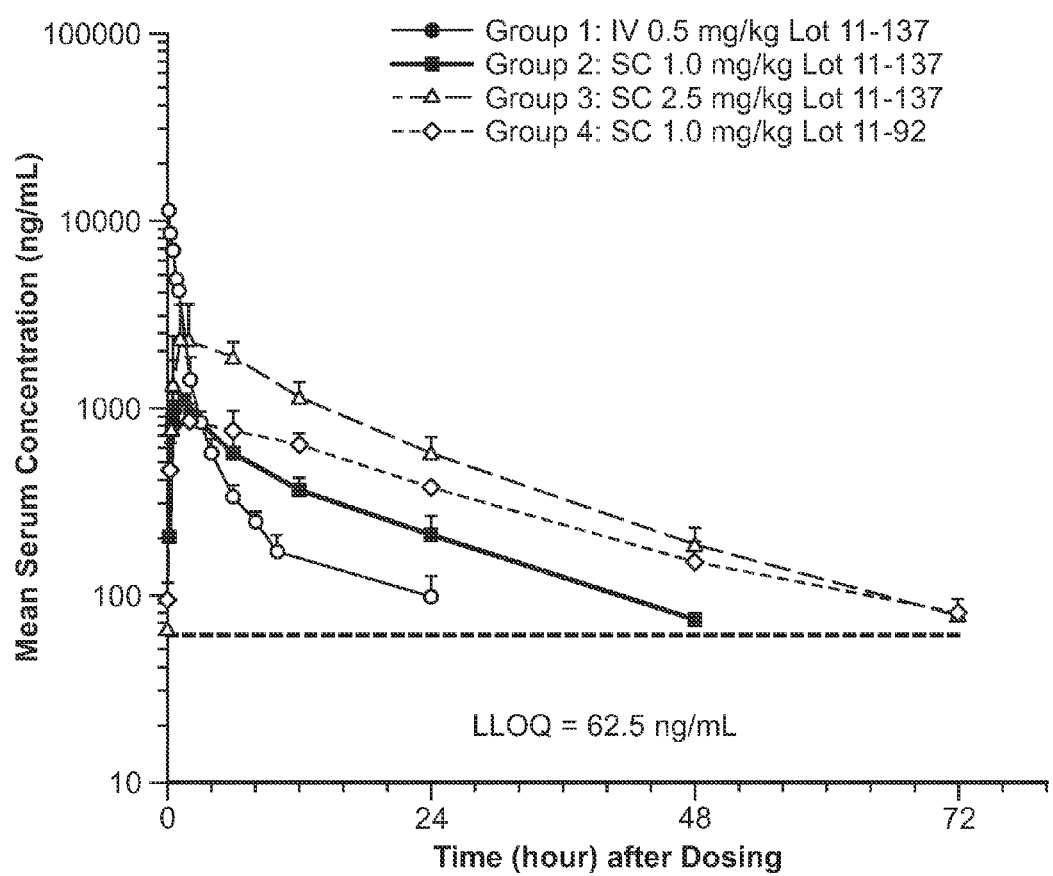
FIG. 15 illustrates exemplary data comparing serum concentration as a function of time in Gottingen minipigs, for four different experimental treatment groups (G1-G4).

These data demonstrate that SC injection at both the 1.0 mg/kg and 2.5 mg/kg doses, were taken up directly into the circulating blood supply; reaching a peak concentration approximately 4 hours after administration. Contrary to IV injection rI2S administered by subcutaneous injection remained in the blood supply for a longer duration of time, with serum rI2S levels detected as far out as 72 hours post injection (FIG. 15). Furthermore, the data demonstrates consistent trends within the pharmacokinetic parameters for each of the 1.0 and 2.5 mg/kg SC groups, despite minor lot to lot variability. Thus demonstrating reproducible delivery and clinical efficacy for SC administration of rI2S, supporting its potential use in treating a subject suffering from a lysosomal storage disease.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

The invention claimed is:

1. A method for treating Hunter syndrome comprising administering subcutaneously to a subject suffering from or susceptible to Hunter syndrome a therapeutically effective dose of a replacement iduronate-2-sulfatase (I2S) protein in a range from 0.5 mg/kg to 10 mg/kg body weight in a volume of less than 5 ml periodically at an administration interval such that at least one symptom or feature of Hunter syndrome is reduced in intensity, severity, or frequency, or has delayed onset.

2. The method of claim 1, wherein the step of administering subcutaneously comprises administering the replacement I2S protein at a subcutaneous tissue selected from the group consisting of thigh region, upper arm, abdominal region, gluteal region, and scapular region of the subject.

3. The method of claim 1, wherein the therapeutically effective dose is in a range from about 0.5 mg/kg to 2.5 mg/kg body weight.

4. The method of claim 1, wherein the therapeutically effective dose is sufficient to achieve serum concentration of the replacement I2S protein within a range from about 10 ng/ml to 10,000 ng/ml within 24 hours following administration to the subject.

5. The method of claim 1, wherein the therapeutically effective dose is sufficient to achieve the average maximum serum concentration ($C_{max}$) following a single administration of greater than about 1.5 μg/ml.

6. The method of claim 1, wherein the therapeutically effective dose is sufficient to achieve an average area under the concentration-time curve (AUC) following a single administration of greater than about 200 min* μg/ml.

7. The method of claim 1, wherein the administration interval is daily, twice a week, weekly, bi-weekly, monthly, or once every two months.

8. The method of claim 1, wherein the administration interval is longer than a week.

9. The method of claim 1, wherein the replacement I2S protein is administered at a concentration greater than 10 mg/ml.

10. The method of claim 1, wherein the replacement I2S protein is administered in a saline solution.

11. The method of claim 10, wherein the saline solution comprises a surfactant.

12. The method of claim 11, wherein the surfactant is selected from the group consisting of polysorbate 20, polysorbate 40, polysorbate 60, polysorbate 80 and combinations thereof.

13. The method of claim 10, wherein the saline solution has a pH ranging from approximately 3-8.

14. The method of claim 1, wherein the step of subcutaneous administration results in systemic delivery of the replacement I2S protein in one or more target tissues.

15. The method of claim 14, wherein the one or more target tissues are selected from muscle, skin, liver, kidney, spleen, joints, bone, lung and airways, tongue, upper respiratory tract, eye, ear, connective tissue and heart.

16. The method of claim 14, wherein the step of subcutaneous administration results in increased I2S protein enzymatic level and/or activity in the one or more target tissues.

17. The method of claim 16, wherein the increased enzymatic level or activity in the one or more target tissues is at least approximately 10% of normal I2S enzymatic level or activity.

18. The method of claim 1, wherein the step of subcutaneous administration results in reduction of GAG level in serum, urine or target tissues.

19. The method of claim 18, wherein the GAG level is reduced by at least 20%, 40%, 50%, 60%, 80%, 90%, 1-fold, 1.5-fold, or 2-fold as compared to a control.

20. The method of claim 1, wherein the step of subcutaneous administration results in reduced size of liver and/or spleen.

21. The method of claim 20, wherein the size of liver and/or spleen is reduced by at least 10%, 20%, 40%, 50%, 60%, 80%, 90%, 1-fold, 1.5-fold, or 2-fold as compared to a control.

22. The method of claim 1, wherein the step of subcutaneous administration results in improved walking capacity in the subject.

23. The method of claim 22, wherein the walking capacity is improved by, on average, at least 10 meters, 15 meters, 20 meters, 25 meters, 30 meters, 35 meters, 40 meters, 45 meters, 50 meters, 55 meters, 60 meters, 65 meters, 70 meters, 75 meters, 80 meters, 85 meters, 90 meters, 95 meters, 100 meters, 110 meters, 120 meters, 130 meters, 140 meters, 150 meters, 160 meters, 170 meters, 180 meters, 190 meters, 200 meters, 210 meters, 220 meters, 230 meters, 240 meters, 250 meters, as determined by the 6-Minute Walk Test as compared to a control.

24. The method of claim 1, wherein the I2S protein comprises amino acid sequence of SEQ ID NO:1.

* * * * *

SEQUENCE LISTING

```
<160> NUMBER OF SEQ ID NOS: 4

<210> SEQ ID NO 1
<211> LENGTH: 525
<212> TYPE: PRT
<213> ORGANISM: Homo sapiens

<400> SEQUENCE: 1

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
```

```
                  165                 170                 175
Thr Glu Gln Ala Ile Gln Leu Leu Glu Lys Met Lys Thr Ser Ala Ser
                180                 185                 190

Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
        210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
                260                 265                 270

Gln Ser Tyr Phe Ala Ser Val Ser Tyr Leu Asp Thr Gln Val Gly Arg
            275                 280                 285

Leu Leu Ser Ala Leu Asp Asp Leu Gln Leu Ala Asn Ser Thr Ile Ile
        290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
                340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
        370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
                420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
        450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
                500                 505                 510

Asp Ser Gln Gly Gly Asp Leu Phe Gln Leu Leu Met Pro
            515                 520                 525

<210> SEQ ID NO 2
<211> LENGTH: 550
<212> TYPE: PRT
<213> ORGANISM: Homo sapiens

<400> SEQUENCE: 2

Met Pro Pro Pro Arg Thr Gly Arg Gly Leu Leu Trp Leu Gly Leu Val
1               5                   10                  15
```

```
Leu Ser Ser Val Cys Val Ala Leu Gly Ser Glu Thr Gln Ala Asn Ser
             20                  25                  30

Thr Thr Asp Ala Leu Asn Val Leu Leu Ile Ile Val Asp Asp Leu Arg
         35                  40                  45

Pro Ser Leu Gly Cys Tyr Gly Asp Lys Leu Val Arg Ser Pro Asn Ile
     50                  55                  60

Asp Gln Leu Ala Ser His Ser Leu Leu Phe Gln Asn Ala Phe Ala Gln
 65                  70                  75                  80

Gln Ala Val Cys Ala Pro Ser Arg Val Ser Phe Leu Thr Gly Arg Arg
                 85                  90                  95

Pro Asp Thr Thr Arg Leu Tyr Asp Phe Asn Ser Tyr Trp Arg Val His
             100                 105                 110

Ala Gly Asn Phe Ser Thr Ile Pro Gln Tyr Phe Lys Glu Asn Gly Tyr
         115                 120                 125

Val Thr Met Ser Val Gly Lys Val Phe His Pro Gly Ile Ser Ser Asn
     130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                 165                 170                 175

Glu Leu His Ala Asn Leu Leu Cys Pro Val Asp Val Leu Asp Val Pro
             180                 185                 190

Glu Gly Thr Leu Pro Asp Lys Gln Ser Thr Glu Gln Ala Ile Gln Leu
         195                 200                 205

Leu Glu Lys Met Lys Thr Ser Ala Ser Pro Phe Phe Leu Ala Val Gly
     210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                 245                 250                 255

Asp Gly Leu Pro Pro Val Ala Tyr Asn Pro Trp Met Asp Ile Arg Gln
             260                 265                 270

Arg Glu Asp Val Gln Ala Leu Asn Ile Ser Val Pro Tyr Gly Pro Ile
         275                 280                 285

Pro Val Asp Phe Gln Arg Lys Ile Arg Gln Ser Tyr Phe Ala Ser Val
     290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                 325                 330                 335

Trp Ala Leu Gly Glu His Gly Glu Trp Ala Lys Tyr Ser Asn Phe Asp
             340                 345                 350

Val Ala Thr His Val Pro Leu Ile Phe Tyr Val Pro Gly Arg Thr Ala
         355                 360                 365

Ser Leu Pro Glu Ala Gly Glu Lys Leu Phe Pro Tyr Leu Asp Pro Phe
     370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                 405                 410                 415

Gln Val Pro Pro Arg Cys Pro Val Pro Ser Phe His Val Glu Leu Cys
             420                 425                 430

Arg Glu Gly Lys Asn Leu Leu Lys His Phe Arg Phe Arg Asp Leu Glu
```

```
                435                 440                 445
Glu Asp Pro Tyr Leu Pro Gly Asn Pro Arg Glu Leu Ile Ala Tyr Ser
450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
                500                 505                 510

Asn Phe Ser Asp Ile His Ala Gly Glu Leu Tyr Phe Val Asp Ser Asp
                515                 520                 525

Pro Leu Gln Asp His Asn Met Tyr Asn Asp Ser Gln Gly Gly Asp Leu
530                 535                 540

Phe Gln Leu Leu Met Pro
545                 550

<210> SEQ ID NO 3
<211> LENGTH: 550
<212> TYPE: PRT
<213> ORGANISM: Homo sapiens

<400> SEQUENCE: 3

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
                20                  25                  30

Thr Thr Asp Ala Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
            115                 120                 125

Val Thr Met Ser Val Gly Lys Val Phe His Pro Gly Ile Ser Ser Asn
130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
            195                 200                 205

Leu Glu Lys Met Lys Thr Ser Ala Ser Pro Phe Phe Leu Ala Val Gly
            210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255
```

```
Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Phe Gln Leu Leu Met Pro
545                 550

<210> SEQ ID NO 4
<211> LENGTH: 343
<212> TYPE: PRT
<213> ORGANISM: Homo sapiens

<400> SEQUENCE: 4

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80
```

```
Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Phe Leu Met Arg Thr Asn Thr
            340
```